United States Patent [19]

Schulman et al.

[11] Patent Number: 5,791,344
[45] Date of Patent: *Aug. 11, 1998

[54] PATIENT MONITORING SYSTEM

[75] Inventors: Joseph H. Schulman, Santa Clarita; Ronald J. Lebel, Sherman Oaks; Joseph Y. Lucisano, San Diego; Alfred E. Mann, Beverly Hills; Orville Rey Rule, III; David I. Whitmoyer, both of Los Angeles, all of Calif.

[73] Assignee: Alfred E. Mann Foundation for Scientific Research, Sylmar, Calif.

[*] Notice: The term of this patent shall not extend beyond the expiration date of Pat. No. 5,497,772.

[21] Appl. No.: 582,756

[22] Filed: Jan. 4, 1996

Related U.S. Application Data

[63] Continuation-in-part of Ser. No. 155,737, Nov. 19, 1993, Pat. No. 5,497,772.

[51] Int. Cl.⁶ .................................................. A61B 5/00
[52] U.S. Cl. ........................ 128/635; 204/403; 204/415
[58] Field of Search ........................ 128/635; 604/64–66; 204/403, 408, 412, 415

[56] References Cited

U.S. PATENT DOCUMENTS

| | | | |
|---|---|---|---|
| 3,972,320 | 8/1976 | Kalman | 128/903 |
| 4,151,845 | 5/1979 | Clemens | 128/DIG. 13 |
| 4,431,004 | 2/1984 | Bessman et al. | 128/635 |
| 4,522,690 | 6/1985 | Venkatasetty | 204/415 |
| 4,627,906 | 12/1986 | Gough | 204/415 |
| 4,650,547 | 3/1987 | Gough | 204/1 T |
| 4,671,288 | 6/1987 | Gough | 128/635 |
| 4,703,756 | 11/1987 | Gough et al. | 123/635 |
| 4,759,828 | 7/1988 | Young | 204/415 |
| 4,781,798 | 11/1988 | Gough | 204/1 T |
| 4,796,634 | 1/1989 | Huntsmen | 128/662.01 |
| 4,815,469 | 3/1989 | Cohen et al. | 128/634 |
| 4,832,797 | 5/1989 | Vadgama et al. | 204/415 |
| 4,871,351 | 10/1989 | Feingold | 604/66 |
| 4,890,620 | 1/1990 | Gough | 128/635 |
| 4,891,104 | 1/1990 | Liston et al. | 204/415 |
| 4,934,369 | 6/1990 | Maxwell | 128/637 |
| 4,944,299 | 7/1990 | Silvian | 128/419 |
| 4,954,129 | 9/1990 | Guiliani et al. | 604/53 |
| 5,030,333 | 7/1991 | Clarke, Jr. | 128/635 |
| 5,135,003 | 8/1992 | Souma | 128/680 |
| 5,190,041 | 3/1993 | Palti | 604/66 |
| 5,271,815 | 12/1993 | Wang | 204/415 |
| 5,320,098 | 6/1994 | Davidson | 128/908 |
| 5,322,063 | 6/1994 | Allen et al. | 204/412 |
| 5,496,453 | 3/1996 | Uenoyama et al | 204/415 |

*Primary Examiner*—Robert L. Nasser
*Attorney, Agent, or Firm*—Fitch, Even, Tabin & Flannery

[57] ABSTRACT

A patient monitoring system measures the concentration of a particular substance in a patient's tissue, blood, or other bodily fluids, provides an indication of the rate of change of such concentration, and determines whether the measured concentration and rate of change are within certain preset limits. If not, an audible and/or visual alarm signal is generated. The patient monitoring system includes at least one enzymatic sensor adapted to be inserted into the patient, where it produces sensor signals related to the concentration of the substance being measured. The sensor signals are delivered through a suitable interconnect cable to a monitor. In one embodiment, the interconnect cable includes a contactless connector that electrically isolates the enzymatic sensor from the monitor, and reduces the number of conductors required to interface with a plurality of sensors. The monitor interprets the sensor signals by applying a previously determined calibration to quantitatively determine the substance concentration value. The substance concentration value thus determined is then processed in order to determine the rate of change, is stored (to create a history or record), and may also be displayed in large, easy-to-read numerals. Rate of change information (trend) may also be numerically or graphically displayed.

33 Claims, 12 Drawing Sheets

```
SHOW MARKERS                    V0.21  09/09/93  16:06:20
```

| 09/09 - HH:MM EXERCISE | ▲ | MENU |
| 09/09 - HH:MM EVENT-1 | | |
| 09/09 - HH:MM EVENT-2 | | |
| 09/09 - HH:MM EVENT-3 | | GRAPH |
| 09/09 - HH:MM INSULIN | ▼ | |
| 09/09 - HH:MM MEAL | | |
| 09/09 - HH:MM SLEEP | | 212 |
| 09/09 - HH:MM EXERCISE | | |
| 09/09 - HH:MM EVENT-1 | | |
| 09/09 - HH:MM EVENT-2 | | |
| 09/09 - HH:MM EVENT-3 | | ↑ 24 mg/dL/hr |
| 09/09 - HH:MM INSULIN | | |
| 09/09 - HH:MM MEAL | | |
| 09/09 - HH:MM SLEEP | | |
| 09/09 - HH:MM EXERCISE | | |

| Name: SMITH, JOHN | HIGH 300 mg/dL |
| Sensor: --------------- | LOW   50 mg/dL |
| WAITING FOR LAB RESULT | TREND     OFF |

*FIG. 10D*

```
OPTIONS MENU                    V0.21  09/09/93  16:03:35
SELECT OPTION
```

| INFO | | | MENU |
| CHOOSE UNITS | CHOOSE LANG | DIAG | |
| DATE FORMAT | SET CLOCK | SELF TEST | GRAPH |

258

↑ 30 mg/dL/hr

| Name: SMITH, JOHN | HIGH 300 mg/dL |
| Sensor: --------------- | LOW   50 mg/dL |
| Next Cal. 09/10 16:00 | TREND     OFF |

*FIG. 10E*

PATIENT MONITORING SYSTEM

This is a continuation-in-part application of patent application, Ser. No. 08/155,737, filed Nov. 19, 1993, now U.S. Pat. No. 5,497,772.

BACKGROUND OF THE INVENTION

The present invention relates to patient monitoring systems and methods, and more particularly to a system that monitors the amount and rate of change of a specified substance, e.g., glucose, in a patient, providing an easy-to-read display of such monitored information, as well as an alarm if either the amount or rate of change exceeds programmable limits.

The monitoring and measuring of glucose concentrations in a patient's blood is one application of the present invention. Glucose is a simple sugar containing six carbon atoms (a hexose). Glucose is an important source of energy in the body and the sole source of energy for the brain. Glucose is stored in the body in the form of glycogen. In a healthy person, the concentration of glucose in the blood is maintained at around 5 mmol/l by a variety of hormones, principally insulin and glucagon. If the blood-glucose concentration falls below this level neurological and other symptoms may result, such as hypoglycemia. Conversely, if the blood-glucose level is raised above its normal level, e.g., to above about 10 mmol/l, the condition of hyperglycemia develops, which is one of the symptoms of diabetes mellitus. It is thus evident that maintaining the concentration of glucose in the blood at a proper level is critically important for wellness and good health.

Unfortunately, some individuals, either through disease, dramatic and/or sudden changes to the body (such as may be caused by injury or surgery), or for other reasons, are unable to maintain the proper level of glucose in their blood. In such instances, the amount of glucose can usually be altered, as required, in order to bring the glucose concentration to a proper level. A shot of insulin, for example, can be administered in order to decrease the glucose concentration (insulin decreases the amount of glucose in the blood). Conversely, glucose may be added directly to the blood through injection, an intravenous (IV) solution, or indirectly by eating or drinking certain foods or liquids.

Before the glucose concentration can be properly adjusted, however, an attending physician (or the patient himself or herself), must know what the present glucose concentration is and whether such concentration is increasing or decreasing. Unfortunately, the only viable technique heretofore available for measuring glucose concentration has been by drawing a blood sample and directly measuring the amount of glucose therein, or by measuring the amount of sugar in the urine. Both measurement techniques are not only inconvenient for the patient, but also may require significant time, manpower, and the use of expensive laboratory instruments, tools or aides to complete. As a result, it is usually not possible for a physician to know immediately what the glucose concentration of a given patient is. Rather, fluid samples must first be obtained, tested or analyzed, and a report issued. Based on such report, appropriate corrective action can then be taken when needed, e.g., through insulin injections or IV supplements, to move the glucose concentration back to an acceptable level. Unfortunately, however, because of the inherent time delay involved with gathering the fluid samples, performing the analysis, and issuing the report, such corrective action may not be possible until several hours after it is first needed. Even after the report is issued, the report results may be misinterpreted, or (e.g., through transcription or analysis error) may simply be wrong. Hence, it is apparent that what is needed is a way to accurately determine the glucose concentration of a patient immediately, effectively communicate such measured concentration to a physician or other interested person (including the patient) with minimum likelihood of error, and provide a clear indication of whether such concentration is within certain prescribed safe limits.

Even after the glucose concentration is known, the physician must still estimate how much corrective action is required until such time as a direction and rate of change of the glucose concentration level has been established. Unfortunately, to identify a trend in the glucose concentration using existing techniques, i.e., to determine whether the glucose concentration is increasing or decreasing, and at what rate, a series of the above-described body fluid measurements must first be made, and the results then analyzed. Such measuring and analyzing process only further delays any appropriate corrective action. What is clearly needed, therefore, is a glucose measurement system that provides a physician, or other medical personnel (or the patient himself or herself) with a rapid measure or indication of the rate of change of the glucose concentration, thereby immediately informing the physician whether any corrective action is needed.

In addition to glucose, there are other substances or elements within a patient that need to be monitored for medical or other reasons. There is thus a need in the art for measurement systems that accurately and rapidly not only measure such other substances, but also provide an indication of the rate of change or such measured substances. The present invention advantageously addresses the above and other needs.

SUMMARY OF THE INVENTION

The present invention provides a patient monitoring system that continuously measures the concentration of a specified substance, e.g., glucose, in a patient, and provides an indication of the rate of change of such concentration. The system further automatically determines whether the measured concentration and rate of change are within certain preset limits, and if not, generates an alarm signal.

The preferred embodiment of the invention relates to a monitoring system that continuously measures the glucose concentration in the blood of a patient. However, it is to be understood that the invention is not so limited, but also applies to systems, apparatus, and methods for monitoring and measuring the concentration of any substance or element found in a patient's tissue, blood, or other body fluids that needs to be monitored and measured with an appropriate sensor.

The preferred glucose monitoring system includes a glucose sensor that may be inserted into an appropriate body location, such as the venous system, the peritoneal system, or other location of the patient, where it responds to blood glucose or other elements or substances and produces electrical signals that are related to the concentration of glucose or other substances. The electrical signals generated by the sensor ("sensor signals") are delivered through a suitable interconnect cable to a monitor. The monitor interprets the sensor signals by applying a previously determined calibration to quantitatively determine the concentration value of the blood glucose or other substance. The concentration value thus determined is then processed in order to determine the rate of change, is stored (to create a history or record), and may also be displayed. One selectable display mode displays the measured concentration in large, easy-to-read numerals, with selectable units, e.g., milligrams (mg) per deciliter (dl), or mg/dl. Another selectable display mode displays a graph of the rate of change (trend) in accordance with selected units, such as mg/dl/hr. Such graph provides an easy-to-see representation of the concentration values over a past period of time, e.g., three hours.

The preferred glucose monitor stores the blood glucose value and other data (including the patient name, sensor identification number, start date, etc.) in memory and displays the measured glucose level, updating the displayed level periodically (e.g., once per minute). Such stored data may also advantageously be viewed, as selected, as a graphic display that indicates the last several hours of recorded values, thereby clearly showing any trends in the data over such time period.

In accordance with one aspect of the invention, a plurality of glucose or other sensors, e.g., at least two sensors, are inserted into a vein or other appropriate location of the patient and are coupled to the monitor, with a concentration measurement being provided by each sensor. A prescribed degree of correlation must exist between the readings from each sensor in order to validate the correctness of the concentration measurement that is made. If the prescribed degree of correlation does not exist, then the monitor automatically indicates that a recalibration and/or new sensor(s) is required.

In accordance with a further aspect of the invention, some of the plurality of sensors coupled to the monitor may be other than glucose sensors, e.g., a sensor to detect oxygen, hydrogen peroxide, or other substances or elements of interest that are present in the patient's tissue, blood, or other bodily fluids. The monitor, in such instances, may process and combine the measurements from each sensor, e.g., by combining the measurement from one sensor with the measurement from another sensor, as required, in order to provide an overall evaluation of the condition, well-being and/or health of the patient.

In accordance with another aspect of the invention, the monitor includes a data card port that allows the current data to be stored in a data card that can be selectively removed from the monitor in order to indirectly make such data available to another computer or processor, or to make such data available for analysis at a later time. The monitor may further include, in one embodiment, an RS-232 (serial) port that allows the monitor to be connected directly to a computer network, or other computer equipment, to facilitate the direct transfer of the data to such other computer network or equipment.

In accordance with an additional aspect of the invention, the monitor is controlled via on-screen menus that define the various subroutines or processes carried out by the monitor at any given time. The screen menus are readily accessed, in a preferred embodiment, by simply touching a designated area of a touch sensitive screen. A user of the monitor may readily "jump" between the main menu and any of the subroutines or processes by merely pressing or touching an appropriate MENU button or key displayed on the touch sensitive screen.

In accordance with yet a further aspect of the invention, the patient monitoring system is calibrated with each new sensor. Further, periodically, e.g., once every 24 hours, the system is calibrated against a blood or other tissue sample that has been independently analyzed by a certified reference method for measuring the concentration of a particular element or substance, e.g., glucose, therein.

It is therefore a feature of the invention to provide a monitoring system that continuously monitors the concentration of a specified substance or element within a patient, providing real-time readings and a history of concentration levels of that substance or element for the patient, including the rate at which the concentration is changing. Such system is particularly suited for use in a hospital environment or other in-patient setting. Such system is also adaptable to any language or units of measure.

It is another feature of the invention to provide such a monitoring system that displays the measured concentration in large, easy-to-read numerals that can be seen from across the room, or even from outside of the room (e.g., just by looking into the room where the patient is situated).

It is an additional feature of the invention to provide such a monitoring system that has setable limits above or below which the measured concentration, or the rate of change (trend) of the concentration, may not go without flashing and/or sounding an alarm.

It is a further feature of the invention to provide a glucose or other sensor that is designed to be implanted in the patient, e.g., into the venous system, the peritoneal system, or exposed to other tissue or fluids of the patient, to continuously monitor the presence of a specified substance, e.g., the glucose concentration, and to provide a measurement thereof without having to withdraw a blood or tissue sample (except for an occasional calibration check). Such sensor advantageously provides electrical signals (an electrical current) from which the concentration can be derived.

It is another feature of the invention, in accordance with one embodiment thereof, to provide a monitoring system that couples an implanted or external sensor, e.g., a sensor placed in the venous or peritoneal system of a patient, through a "contactless" connector and two- or three-conductor cable with a monitor. Advantageously, the contactless connector may be purposefully or inadvertently disconnected without harming the patient or the sensor, and without disrupting operation of the sensor (thereby preventing the need for restabilization or recalibration).

It is yet an additional feature of the invention to provide a monitoring system that monitors the blood or other tissue/fluids for the presence of certain substances, and that utilizes the measurements from a plurality of venous, interperitoneal, or other implanted sensors, in order to confirm the correctness of a given determination or measurement. Such system requires, e.g., that the measurements from two or three separate sensors be within certain prescribed limits of each other before a measurement is considered accurate or reliable, or before identifying or confirming the presence and/or concentration of certain substances within the blood or other tissue.

BRIEF DESCRIPTION OF THE DRAWINGS

The above and other aspects, features and advantages of the present invention will be more apparent from the following more particular description thereof, presented in conjunction with the following drawings and appendices wherein:

FIG. 10D shows a representative marker screen that is displayed by the glucose monitor when the marker selection is made from the main menu;

FIG. 10E illustrates the options menu screen that is displayed by the glucose monitor when the options selection is made from the main menu;

Figure 1:
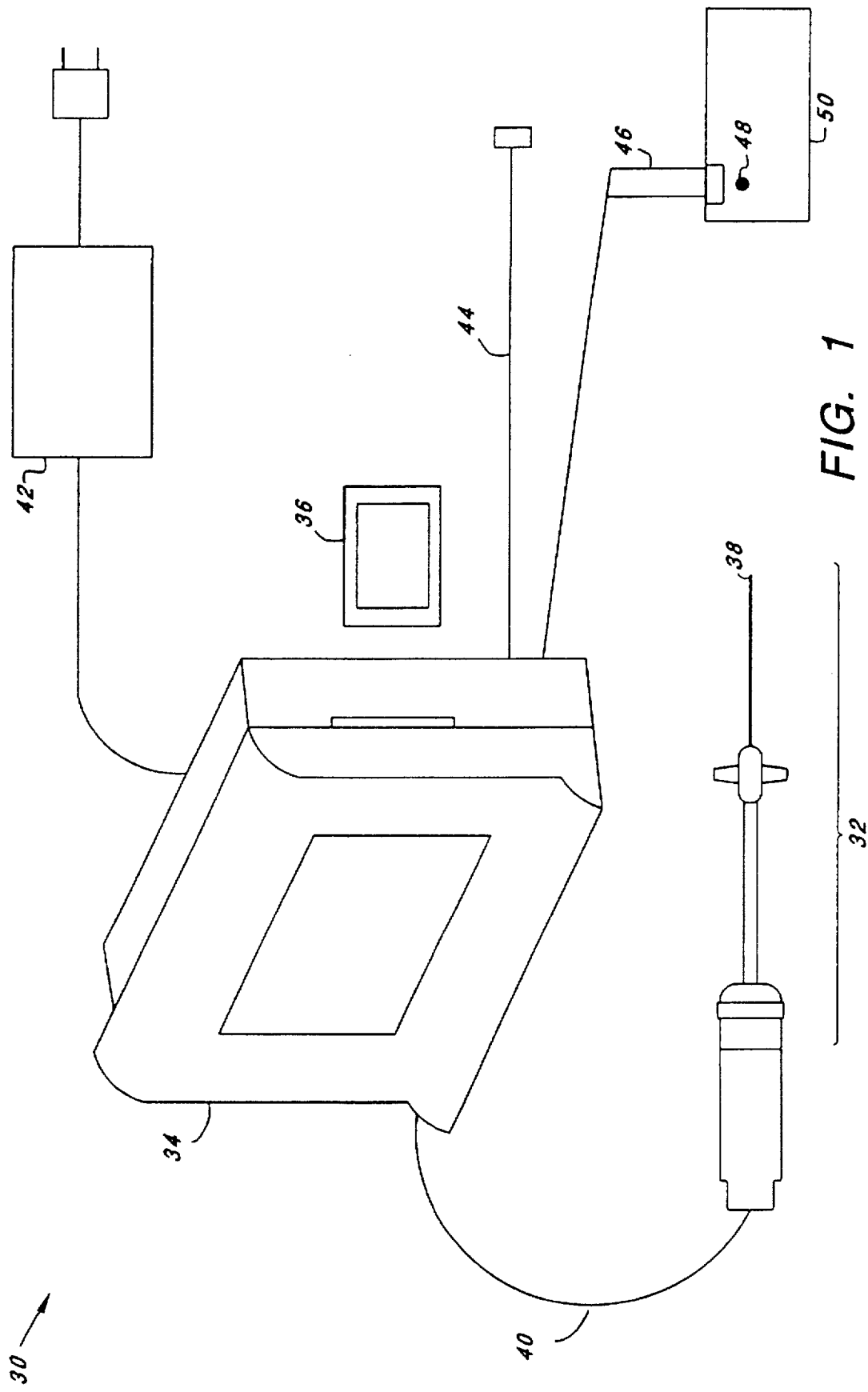
FIG. 1 is a block diagram of a glucose monitoring system made in accordance with the present invention.

Additional information relative to a preferred Glucose Monitoring System may be found in the Appendices of U.S. patent application, Ser. No. 08/155,737, U.S. Pat. No. 5,497,772 entitle "Glucose Monitoring System," filed Nov. 19, 1993, which application is incorporated herein by reference.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

As indicated previously, the present invention relates to a patient monitoring system for monitoring and measuring the concentration of a specified substance or element in the patient's tissue, blood, or other bodily fluids. The preferred embodiment of the invention, described below, relates to a glucose monitoring system that uses one or more glucose sensors inserted into the patient's venous system. However, it is to be understood that the invention is not limited to a glucose monitoring system, but may be used for any application wherein specified substances or elements within a patient's body need to be monitored or measured.

Referring first to FIG. 1, there is shown a block diagram of a glucose monitoring system 30 made in accordance with the present invention. The system 30 includes a glucose sensor assembly 32, a glucose monitor 34 and a removable data card 36. A distal tip 38 of the sensor assembly 32 includes a pair of glucose sensors, described below. The distal tip 38 of the sensor assembly 32 is adapted for insertion into a vein (or other body location) of a patient whose blood glucose concentration is to be measured. The sensor assembly 32 is electrically connected to the glucose monitor 34 by means of an interconnect cable 40. The monitor is powered by a suitable power supply 42 during normal operation. In the event of a power failure, the monitor includes a backup battery that provides sufficient power to operate for up to four hours (without excessive printing).

As explained more fully below, the glucose monitor 34 includes processing circuits, much like a personal computer, that are programmed by a suitable operating program stored in the memory of the monitor or on the removable data card 36. The data card 36 also provides a means for removable data storage, much like a floppy disk in a personal computer, whereon glucose concentration data measured through the sensor assembly 32 may be stored for later analysis. In some embodiments, a computer industry standard RS-232 serial port, located on the back of the monitor 34, further allows a communication cable 44 to be connected to the monitor 34 so that glucose concentration data, or other data (e.g., diagnostic data), obtained by or associated with the glucose monitoring system may also be downloaded to a computer. As required, such RS-232 serial port further allows necessary programming data to be uploaded to the monitor 34, when required.

The monitor 34 further includes an output connector to which an identifier wand 46 may be connected. The identifier wand 46 is used with some types of sensor assemblies to read a memory chip 48, housed in a round chip package that has the appearance of a "button". Such chip package is placed on a shipping package or carton 50 wherein the sensor assembly 32 is placed during shipping. The memory chip 48 includes calibration data unique to the particular sensor assembly 32, which calibration data is used by the monitor 34 as it processes the signals obtained from the sensor assembly 32 in order to accurately and reliably determine the glucose sensor data. Identifier wands 46 and corresponding identifier memory chips 48 are commercially available products that may be obtained from various manufacturers. Other types of sensor assemblies, as explained below, contain the requisite calibration data stored in a small non-volatile memory, powered by a small battery, that is included as part of the sensor assembly. With such sensor assemblies, the monitor automatically reads the calibration data from the chip when a sensor assembly is attached (coupled) to the monitor.

As evident from FIG. 1, an important element of the monitoring system 30 is the sensor assembly 32, and more particularly the glucose sensors that form a part thereof. In order to better understand how such a glucose sensor operates, reference is next made to FIG. 2A, where there is shown a simplified electrical diagram of a glucose sensor 52. It is noted that there are various types of sensors known in the art, including glucose sensors. See, e.g., U.S. Pat. Nos. 4,484,987; 4,650,547; 4,627,906; 4,671,288; 4,781,798; 4,703,756; and 4,890,620, incorporated herein by reference.

Figure 2A:
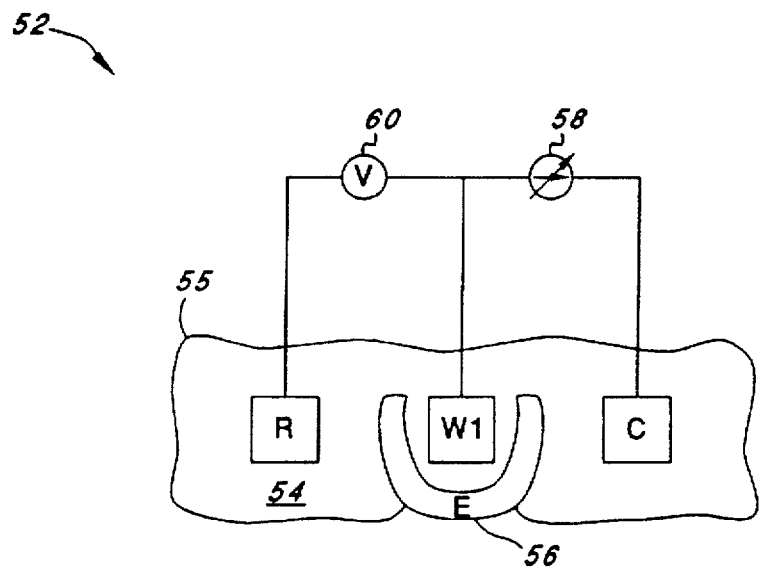
FIG. 2A is an electrical diagram of a glucose sensor.

The glucose sensor 52 of FIG. 2A is based on the "enzyme electrode" principle where an enzyme reaction and an electrochemical detector are utilized to measure the concentration of glucose. The glucose sensor 52 includes at least three electrodes: a first working electrode W1, a counter electrode C, and a reference electrode R, submersed in a suitable conductive liquid 54, such as a saline solution of $H_2O$, confined by a first membrane 55. A fixed trim voltage V is applied between the electrode R and the electrodes W1 and C. A suitable enzyme E is immobilized in a second membrane 56 so as to surround the working electrode W1. For a glucose sensor, the enzyme E is preferably glucose oxidase (GO). During operation, the sensor 52 is inserted in the venous system so that the enzyme E is exposed to the flow of blood. Glucose and oxygen diffuse from the blood into the membranes 55 and 56 wherein, in the presence of the enzyme, they react as follows:

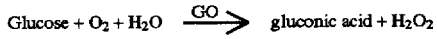

$$Glucose + O_2 + H_2O \xrightarrow{GO} gluconic\ acid + H_2O_2$$

Figure 2B:
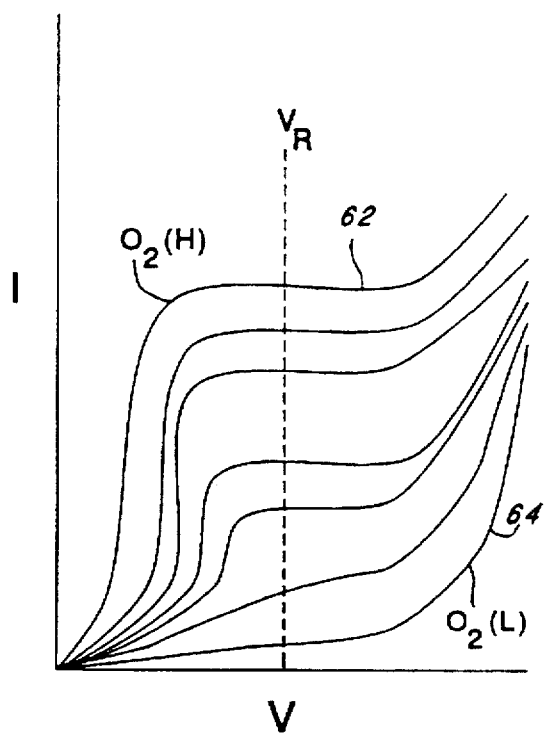
FIG. 2B is a graph that qualitatively depicts the relationship between electrical current delivered to the electrodes of the glucose sensor and the voltage applied between the electrodes varies as a function of oxygen content.

The rate of the above reaction is directly related to the concentration of glucose in the blood and is monitored by an electrochemical oxygen detector made up of the electrodes W1, R and C, the current source 58 and the voltage source 60. The working electrode W1 and the counter electrode C are preferably made or coated from platinum (Pt). The reference electrode R is typically made from or coated with silver chloride, $Ag_2Cl$. When a trim voltage V is placed across the electrodes R and W1, as well as across R and C, a current I tends to flow between the electrodes C and W1. (Assuming the voltage source is an ideal voltage source, with infinite impedance, no current flows through the reference electrode R.) When the above chemical reaction occurs, oxygen is consumed at the working electrode. The amount of oxygen remaining can be determined as a function of the amount of current flowing through the working electrode. More particularly, it can be shown that the relationship between the current (I) that flows and the trim voltage (V) varies as a function of the oxygen concentration as shown qualitatively in FIG. 2B. For a high concentration of $O_2$, a curve 62 establishes the relationship between I and V. For a low concentration of $O_2$, a lower curve 64 establishes the relationship between I and V. For each value of $O_2$ concentration between the high concentration curve 62 and the low concentration curve 64, another curve (intermediate the curves 62 and 64) establishes the current-voltage relationship. Thus, a family of curves exists that establishes the current-voltage relationship, with each curve of the family corresponding to a different $O_2$ concentration.

Figure 2C:
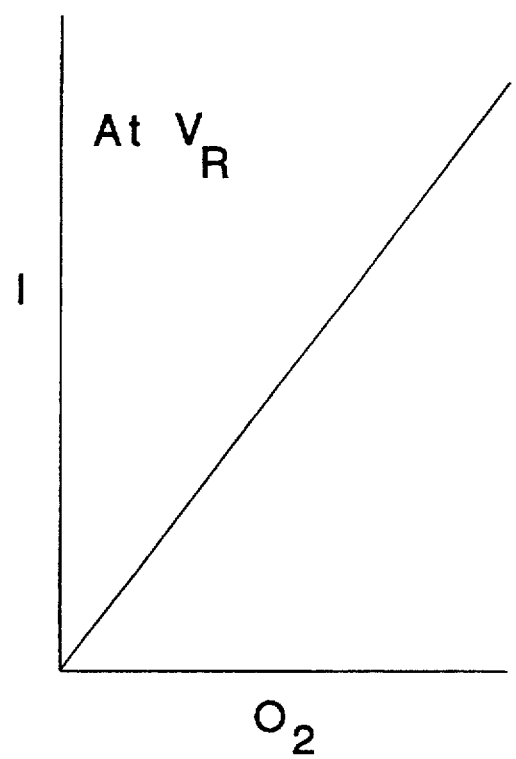
FIG. 2C is a graph that qualitatively depicts the approximatly linear relationship that exists at a fixed electrode voltage between the electrical current passing through the electrode of the glucose sensor and the oxygen concentration.

To measure the $O_2$ concentration using a circuit such as is shown in FIG. 2A, all that need be done is to force the trim voltage V to be a fixed value $V_R$, where $V_R$ typically ranges between 0.3 and 0.7 volts, e.g., 0.5 volts. This is done by adjusting the current I until the desired trim voltage $V_R$ is obtained. At the voltage $V_R$, the relationship between the current I and the oxygen $O_2$ is substantially linear, as depicted qualitatively in FIG. 2C. Thus, using a sensor such as is functionally depicted in FIG. 2A, the amount of oxygen remaining at the working electrode W1 is simply a function of the current I required to force the trim voltage V to $V_R$.

Since the oxygen detector is monitoring the oxygen not consumed by the enzyme reaction, the detector signal, i.e., the current I, is inversely related to the blood glucose concentration. The more glucose in the blood, the less oxygen will be detected by the oxygen detector with the enzyme present.

Figure 3:
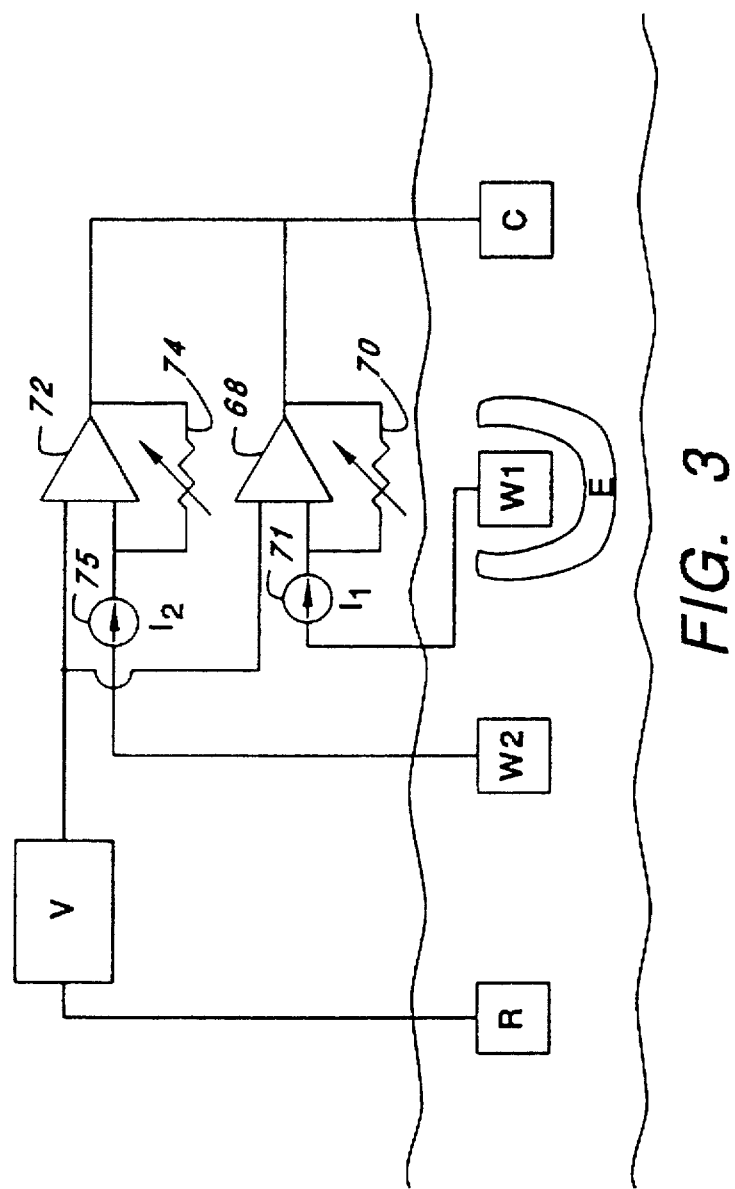
FIG. 3 is an electrical schematic diagram that depicts the use of two working electrodes within the glucose sensor, one to provide a measure of the oxygen that reacts with the glucose in the blood (and thereby used to provide a measure of the glucose in the blood), and another to provide a reference baseline measurement of the background blood oxygen concentration in the blood (used for compensation)

To improve the accuracy of the oxygen determination made by the detector of FIG. 2A, and in particular to allow compensation for changes in the background blood oxygen concentration, a second working electrode W2 is typically employed at a location in the sensor that is not surrounded by the enzyme E, as shown in FIG. 3. As seen in FIG. 3, a first adjustable current source is realized from an operational amplifier 68 and a feedback loop 70. A second adjustable current source is likewise realized from an operational amplifier 72 and a feedback loop 74. Both the first and second current sources apply their respective currents to the counter electrode C. A measurement of the current $I_1$ flowing through the first working electrode W1 is provided by current sensing element 71. Similarly, a measurement of the current $I_2$ flowing through the second working electrode W2 is provided by current sensing element 75.

In operation, the trim voltage V is set to the desired fixed trim value $V_R$, and the currents $I_1$ and $I_2$ are measured. The current $I_1$ provides a measure of the oxygen remaining at the working electrode W1, which in turn provides an inverse measure of the glucose concentration in the blood. The current $I_2$ provides a measure of the background oxygen in the blood, and thus provides a means for compensating the $I_1$ measurement for background oxygen variations. The absolute quantitative value of the blood glucose level is determined by comparison of the two detector signals, i.e., the two currents $I_1$ and $I_2$, and by reference to a previously determined calibration. Appropriate processing to obtain such quantitative measure of the blood glucose level is performed by the processing circuits in the glucose monitor 34 (FIG. 1).

Figure 4A:
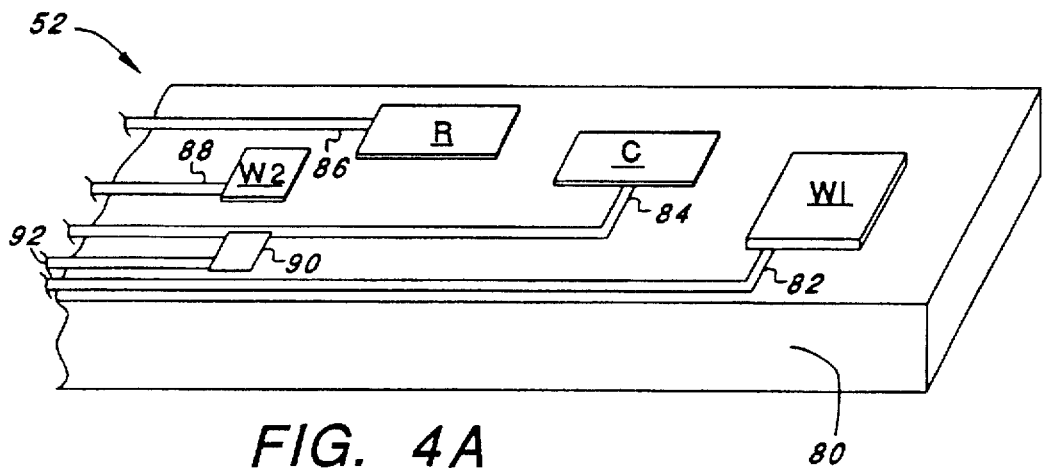
FIG. 4A is a top view of a representative glucose sensor that may be used by the glucose monitoring system of the present invention.
Figure 4B:
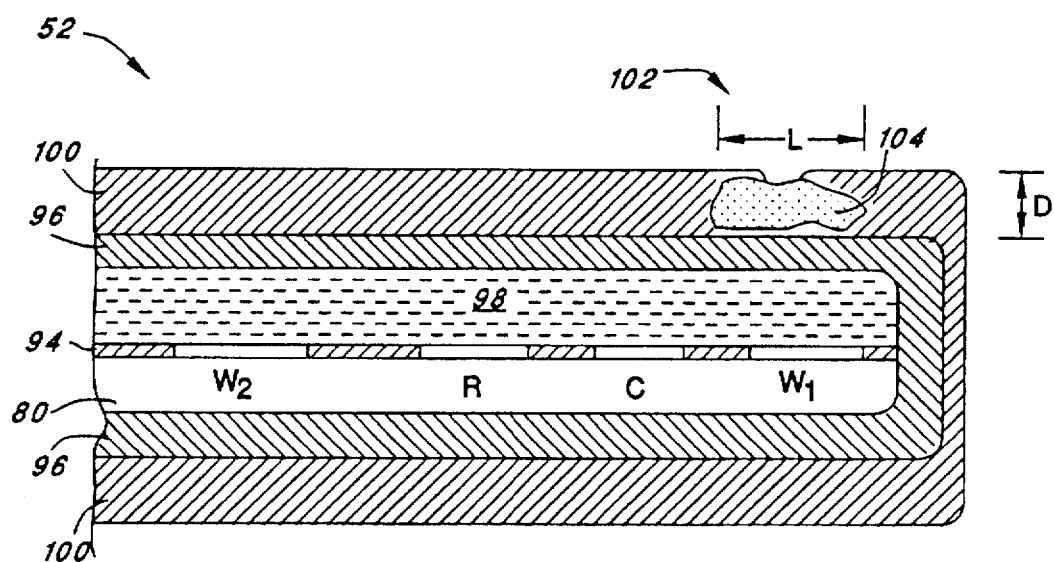
FIG. 4B is a side view of the sensor of FIG. 4A.

Turning next to FIGS. 4A and 4B, there is shown a diagrammatic top view and side view, respectively, of a representative glucose sensor 52 that may be used by the glucose monitoring system 30 of the present invention. The sensor is fabricated on a suitable ceramic substrate 80. Appropriate metalized patterns are deposited or etched on the substrate 80 using conventional thin film deposition, or metalized etching techniques, as are common in the printed circuit board and integrated circuit fabrication arts.

In FIG. 4A, for example, the working electrode W1 is placed near one end of the substrate area used for the sensor 52. A metalized trace 82 provides an electrical connection to this working electrode. The counter electrode C is likewise placed on the substrate, near the working electrode W1. Another metalized trace 84 provides electrical connection to the counter electrode. The reference electrode R is similarly placed on the substrate at a location near the counter electrode C. A metalized trace 86 provides the electrical connection to such reference electrode R. The second working electrode W2 is placed on the substrate adjacent the reference electrode R. A metalized trace 88 provides the electrical connection to the second working electrode W2. Finally, a suitable semiconductor element 90, such as a germanium chip, is placed so as to be in electrical contact with the metalized trace 84 and another metalized trace 92. Such element 90 is used as a temperature sensor. That is, the resistivity of the semiconductor chip 90 is highly dependent upon temperature, and the temperature may thus be monitored by measuring the current that flows through the chip 90 when a fixed voltage is applied across the traces 92 and 84. After stabilization, such temperature of the sensor will be the same as the patient's blood temperature, which is a very useful medical parameter, particularly when it is available continuously. Such temperature measurement may likewise be stored, plotted, graphed or used for other purposes. Other types of temperature sensors, other than a semiconductor chip, may also be mounted on the substrate and used in a similar manner.

As required, a thin layer of titanium, e.g., about 300 Å thick, may be used to bond the metalized patterns to the substrate. The metalized patterns are typically made from, or plated with, the metals indicated above. The patterns are on the order of 1 to 3 mils thick. Note that a complete sensor 52, including a temperature sensor, requires 5 conductors (traces) or wires in order to make the proper electrical connections with the various electrodes and elements. The conductor or trace 84, connected to the counter electrode C and to one side of the temperature sensing element 90, may function as a common conductor.

The sensor 52 shown in FIG. 4A only shows the substrate, electrodes, temperature sensor, and connecting traces. A complete glucose sensor made in accordance with the invention includes more than just these elements. The additional elements required by the sensor 52 are shown in the side view of the sensor in FIG. 4B. As seen in FIG. 4B, a suitable layer of insulation 94, such as glass or aluminum oxide, $AlO_2$, is placed between the electrodes W2, W1, C and R, and between the metalized traces. A thin sheath 96 of silicone rubber, e.g., 0.003 inches thick (3 mils), covers the substrate electrodes and traces. This sheath functions as the membrane 55 referenced in FIG. 2A. A suitable thin pocket or space exists within the sheath 96, above the electrodes, wherein a suitable conductive fluid 98 may be placed. Such space is on the order of 1 to 3 mils thick, and is filled with a thick "jello" like substance known as "hema", that functions as a conductive solution. The thin inner sheath 96 is covered with a second, much thicker, sheath 100, also made of silicone rubber, or equivalent substance. A pocket, or "window", 102 is formed in the outer sheath 100 over the first working electrode W1. Such pocket 102 is filled with the enzyme glucose oxidase (GO) 104. The pocket wherein the enzyme 104 is placed has a length L and a thickness D, as shown in the figure. It is preferred that the ratio between L and D be on the order of about 3 to 1 in order to provide the best linearity between the current $I_1$ and the glucose concentration measurement. However, this ratio may vary widely from the preferred 3 to 1 ratio and the sensor will still function.

In operation, the silicone rubber sheaths 96 and 100 comprise membranes through which $O_2$ may pass. Thus, when the entire sensor is inserted in the venous or peritoneal system, the oxygen and glucose in the blood are able to pass into the packet 102 and contact enzyme 104 where the above-described chemical reaction takes place. Excess, unreacted and background oxygen can then be determined allowing the oxygen to be measured by measuring the currents $I_1$ and $I_2$, from which the glucose concentration can be determined.

Typically, at least two, and perhaps three, or more, sensors as shown in FIGS. 4A and 4B may be included within the same glucose sensor assembly 32 (FIG. 1). When such multiple sensors are used, they may be fabricated on the same substrate, with the respective "windows" (or pockets wherein the enzyme is placed above the first working electrode) being spaced apart about 0.4 to 1.0 inches along the length of the substrate.

Figure 4C:
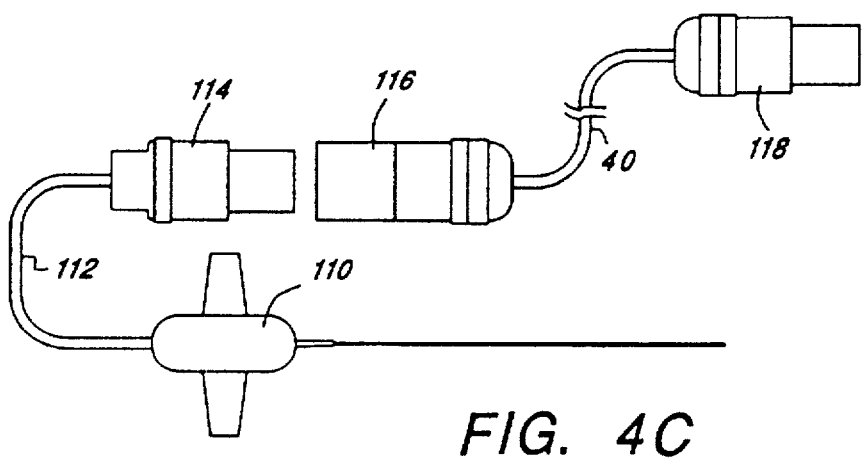
FIG. 4C shows a glucose sensor assembly that includes two glucose sensors of the type shown in FIGS. 4A and 4B, which assembly includes a "butterfly" handle to facilitate attaching the assembly to a patient, and appropriate connectors and cables for connecting the sensor assembly to the glucose monitor.

FIG. 4C illustrates a glucose sensor assembly 32 that includes two glucose sensors 106 and 108 of the type shown in FIGS. 4A and 4B. As seen in FIG. 4C, the two sensors are located near the distal tip of the assembly. Only this area of the assembly includes the substrate within the inner and outer sheaths as described above. The remaining portion of the distal end of the assembly 32 comprises a suitable multi-conductor cable, e.g., 9 or 10 conductor cable, that provides the requisite electrical contact with the 5 conductors or traces of each sensor. (Note, that the two sensors 106 and 108 may share the same "common" line, thereby reducing the number of conductors needed to nine.) Such 9 or 10 conductor cable may be, e.g., a laminated ribbon cable that includes 1 mil conductive wires spaced apart 1–2 mils in a Teflon inner layer, with kapton layers on each side (top and bottom) of the middle Teflon layer.

Figure 5:
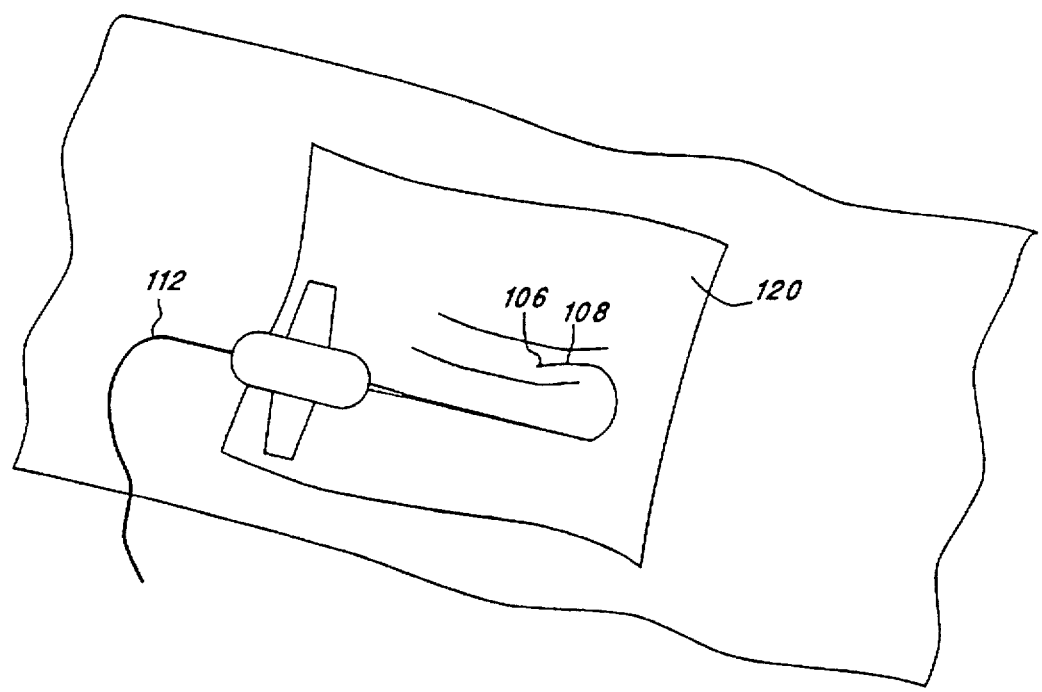
FIG. 5 diagrammatically illustrates a typical dressing placement of the sensor assembly of FIG. 4C in the arm of a patient.

A butterfly handle 110 facilitates attachment of the assembly 32 to a patient, as depicted in FIG. 5 below. From the butterfly handle 110, a multi-conductor cable 112 of about 18 inches carries the 9 or 10 conductors to a suitable male connector 114. An extension cable 40 of about 10 feet in length then provides the electrical connection with the monitor 34. The extension cable 40 is a flexible, low noise, multi-conductor type of cable. The cable 40 is terminated at each end with a uniquely shaped (keyed) electrical connectors. A female connector 116 is adapted to connect with the male connector 114 of the sensor assembly 32. A male connector 118 is adapted to connect with the monitor 34. The cable 40 and its connectors 116 and 118 are designed for multiple connect/disconnects without replacement. The extension cable 40 advantageously allows the monitor 34 to be placed near the patient's bedside, e.g., on a bed pole, yet still allows the patient sufficient movement of his or her arm, where the sensor assembly is typically inserted, so as not to be too restrictive of the patient's movements.

The tip of the sensor assembly 32 may be inserted into the venous system or other body/tissue location using several methods. Typically, the insertion site is sterilized, and an 18 gauge tear-away introducer needle (provided with the sensor assembly) is inserted into a peripheral vein. It is important that the vein selected have sufficient diameter to accommodate the sensor while still allowing blood to flow past the device after it has been inserted. The preferred insertion site in most patients is the antecubital region of the cephalic vein.

After the introducer needle has been inserted into the vein, the sensor is removed from its fluid sheath (in which it is shipped) and the tip of the sensor is kept from contacting any surface in the field. The sensor is inserted through the introducer needle and advanced into the vein about 4 to 6 cm. The introducer is then withdrawn while holding the sensor assembly to prevent its removal. The sensor is looped on the skin to provide strain relief for the insertion site. The loop and the insertion site are then covered with a transparent dressing, and the butterfly handle 110 is included under the dressing, as shown in FIG. 5. The sensor is then ready to be connected to the monitor 34.

Figure 6:
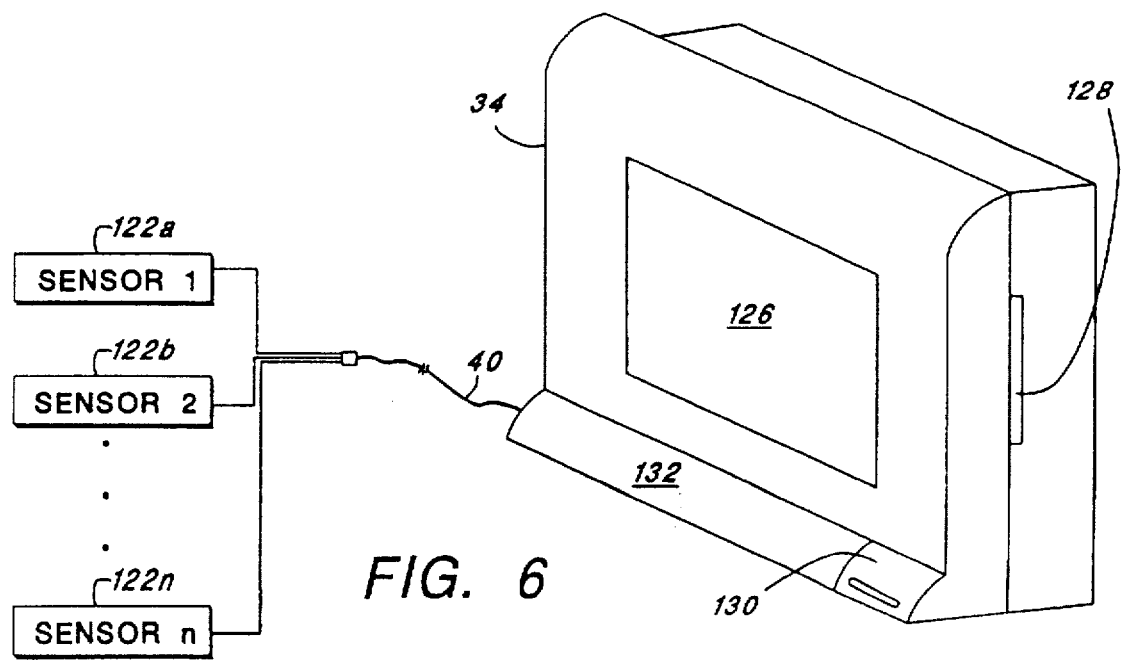
FIG. 6 shows a glucose monitoring system that includes a glucose monitor connected to a plurality of different sensors.

Turning next to FIG. 6, it is seen that the monitoring system of the present invention is not limited to use with one or two sensors. Rather, the monitor 34 may be connected to a plurality of different sensors 122a, 122b, ... 122n. Each sensor may be a glucose sensor as described above, or some other sensor as is known in the art. The monitor 34 obtains glucose sensor readings from each sensor and requires that there be some specified relationship between the sensor readings before such sensor readings are considered to be valid. For example, when two glucose sensors are used, the readings from each sensor are combined, e.g., averaged, to provide the overall or composite glucose measurement value. However, such combining only occurs if the sensor readings are within 10% of each other over a six minute interval. If not, then the monitor 34 requires a recalibration of the sensors to be made. Should the sensor reading be more than 30% different over a six minute interval, then the monitor 34 requests that the sensors be replaced. If at any time the sensor readings are more than 50% different, then the monitor requires that the sensors be replaced.

In addition to using multiple sensors of the same type, e.g., multiple glucose sensors, the monitoring system of the present invention contemplates that the multiple sensors may be of different types. For example, one sensor may sense oxygen, the other may sense peroxide ($H_2O_2$). Note peroxide is one of the products of the reaction that takes place in the presence of the enzyme, and therefore making a peroxide measurement represents an alternate way of determining the glucose concentration. An appropriate relationship between the oxygen measurement defines the glucose concentration. If the sensors give conflicting results, then that indicates something is wrong, e.g., a sensor malfunction or contaminants in the blood or other body tissue.

The oxygen sensor described above in FIGS. 2–4 can readily be converted to a peroxide sensor by simply changing the polarity of the trim voltage that is applied to the reference electrode, and by removing the outer and inner rubber sheaths. (Some means must still be used, of course, to keep the enzyme confined to an area near the working electrode.) Thus, a peroxide sensor has its electrodes exposed so that they come in direct contact with the blood or other body tissue/fluids.

Other types of sensors, i.e., used to detect elements or compounds other than $O_2$ or $H_2O_2$, may be fabricated by using a different enzyme in the vicinity of the first working electrode. Using such other sensors, alone or in various combinations with other sensors, thus provides versatility in how the present monitor may be used to determine an appropriate measurement, or to determine in real-time the presence of a particular substance, element or contaminant in the tissue, blood, or other bodily fluids of the patient.

Still referring to FIG. 6, a preferred representation of the monitor 34 is shown in greater detail. The monitor includes a large screen 126 wherein the sensor data, e.g., glucose concentration, rates of change, and history (graphs of concentration over time) may be displayed. A touch screen overlays the display screen and provides a convenient mechanism for entering various commands and selecting various programmable options for use with the monitor 34. A slot 128 appears on one side of the monitor case wherein the data card 36 (FIG. 1) may be removably inserted. A printer is included within the monitor 34, providing a paper tape output that appears from a slot 130. A removable cover 132 reveals a clip for holding the male connector 118 as it is connected to the monitor 34.

Figure 7A:
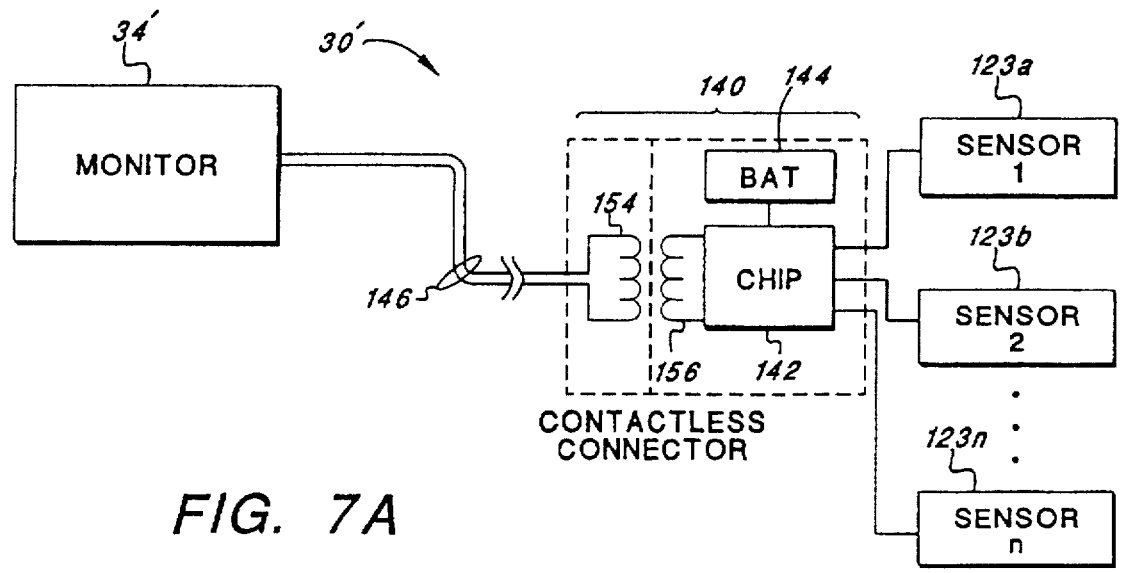
FIG. 7A depicts a glucose monitoring system that is coupled to a plurality of different sensors through a detachable connector that does not use a direct electrical contact (i.e., a "contactless" connector), thereby providing electrical isolation between the glucose monitor and the sensors, and thereby further reducing the number of electrical wires needed within the cable that connects the monitor to the contactless connector.

FIG. 7A depicts a monitoring system 30' having a monitor 34' that is coupled to a plurality of different sensors 123a, 123b, ... 123n through a detachable connector 140 that does not use a direct electrical contact (a "contactless" connector) between the circuits of the monitor 34' and the plurality of sensors 123. Such contactless connector thus provides electrical isolation between the glucose monitor 34' and the sensors 123. Moreover, the contactless connector 140 is a "smart" connector, i.e., it includes a processing chip 142, powered by a battery 144. The processing chip 142 encodes the data being transferred or transmitted from the sensors to the monitor 34'. Such encoding allows address data to be included to identify at which sensor of the plurality of sensors the sensor data originated, and to identify different types of data (e.g., temperature data, $O_2$ data, etc.). Hence, whereas each sensor 123a, 123b, ... 123n requires, e.g., five conductors for proper operation and monitoring, it is possible by encoding the data and sending it over the same conductor to reduce the number of conductors needed within the cable 146 to, e.g., two conductors.

One advantage of the contactless connector 140 shown in FIG. 7A is that the connector 140 can be pulled apart, e.g., purposefully (e.g., when a new sensor is inserted) or inadvertently (e.g., by the patient accidentally moving or pulling his or her arm) without causing harm or damage to either the monitor, sensors, or patient. Typically, the sensors, for proper operation, need to be operated continuously (have a current flowing therethrough, which means the sensors must be "wet") without interruption. Such continuous operation does not require large amounts of power. To the contrary, each sensor usually only requires nanoamperes of current for proper operation. Advantageously, the battery 144 included within the sensor-side of the contactless connector 140 provides such power regardless of whether the connector is coupled to the monitor 34'. Further, such battery 144 may be installed at the factory, and the sensors may thus be operational (assuming they are shipped "wet", i.e., in an appropriate solution) from the time they are shipped, thereby obviating the need for any warm-up or stabilization period after they leave the manufacturing site. Other types of sensors may be operated on a "sampled" basis, which typically requires even less current.

Figure 7B:
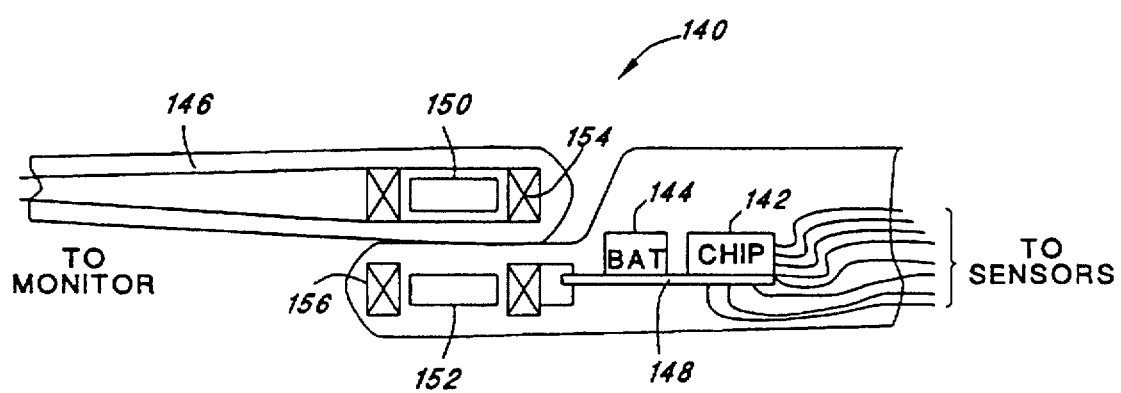
FIG. 7B is a side view of the contactless connector of FIG. 7A.

FIG. 7B is a side view of a representative contactless connector 140. At the end of the cable 146 (the monitor side of the contactless connector 140), there is included a magnet 150 and a coil 154. On the sensor side of the connector 140, there is likewise included a magnet 152 and a coil 156. The magnets 150 and 152 attract each other and force a proper alignment between the coils 154 and 156, and further provide a holding force for holding the connector together (which force is sufficiently strong to maintain the two sides of the connector together, but is not so strong as to prevent the two sides from being pulled apart when desired or needed). The two coils 154 and 156 thus provide transformer (inductive) coupling between the two sides of the connector.

The sensor side of the connector 140 further includes a circuit board 148 on which the battery 144 and the chip 142 are mounted. The chip 142 may be considered as a transmitter chip because it receives all the sensor data from the various sensors, encodes it as required, and transmits it serially through the transformer coupling to the monitor 34'. The chip 142 further includes a small amount of non-volatile memory that is maintained by the battery wherein calibration data is stored.

A significant advantage of utilizing a transmitter chip as described above is that all of the calibration data needed for proper operation may be within the transmitter chip 142. Thus, there is no need to use a wand 46 to read a memory identifier element 48 contained on the shipping package 50. Rather, the monitor will automatically read the calibration data from the chip when a sensor is attached. Further, there is no need for extended stabilization periods to pass before the sensor assembly can be used. All that is required is that the sensor assembly be removed from its shipping carton (which maintains it in a wet environment), be inserted into the venous system or other body location of the patient, and be coupled to the monitor through the contactless connector.

It is noted that while the contactless connector 140 is illustrated in FIGS. 7A and 7B as being realized using transformer coupling, the invention is not intended to be limited to transformer coupling. Other types of contactless coupling, such as optical coupling, may also be used.

Figure 8:
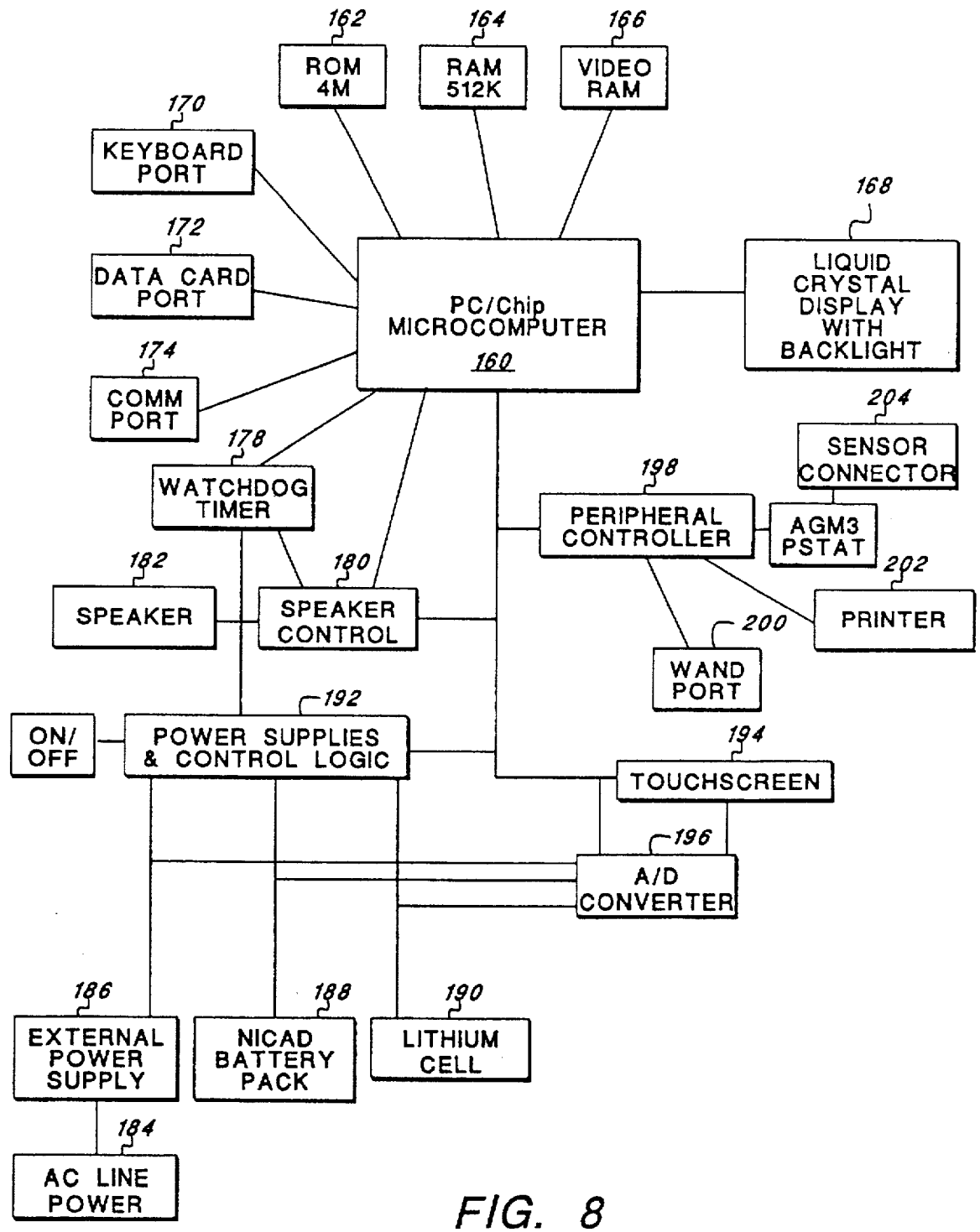
FIG. 8 is a block diagram of one embodiment of a glucose monitor used with the present invention.

Turning next to FIG. 8, there is shown a block diagram of one embodiment of a monitor 34 that may be used with the monitoring system of the invention. The monitor 34 receives sensor signals from the sensor assembly 32 via the interconnect cable 40. It analyzes and stores the concentration level at a prescribed interval, e.g., every minute, in a file named for the sensor number. The file also contains the start date and start time. Such file can be transferred to another computer via the data card 36, or via the RS232 serial port 44, for more extensive analysis.

The monitor 34 displays the current concentration of the substances being monitored and the trend (the rate of change over a previous period of time, e.g., fifteen minutes). The concentration thus measured is presented as either a digital display of the current value, or as a graph. The concentration value is updated once each minute (or other prescribed interval). In the graphic display mode, the concentration is plotted at user selected intervals, showing periods of 3 to 72 hours. The 15 minute trend value is displayed in small numbers in the bottom right portion of each display. Increasing and decreasing trends are indicated with up (↑) and down (↓) arrows, respectively. In the monitor mode, the concentration of the measured substance is displayed in large numerals that can be easily seen from across the room, as illustrated, e.g., in FIG. 10B.

As seen in FIG. 8, at the heart of the monitor 34 is a microcomputer 160. Connected to the microcomputer 160 are a wide array of peripheral devices and circuits. Such devices and circuits include suitable memory, including ROM 162, RAM 164, and a video RAM 166. Also a LCD display 166 is connected to the microcomputer 160, as is a keyboard port 170, a data card port 172, and a comm port (RS-232 serial port) 174. With such peripheral devices, the microcomputer 160 is fully equipped to function as a computer or sophisticated signal processor to perform whatever task it is programmed to perform.

To control the monitor as it performs the function of monitoring the concentration of a specified substance, a monitoring operating program is downloaded, or accessed from, a data card that is inserted into the card port 172. A watchdog timer circuit 178 ensures that all specified events within the operating program occur within specified time limits, else various corrective events are triggered, e.g., putting the monitor into an alarm state where alarms are sounded through a speaker control circuit 180 and speaker 182, and/or flashed on the display 168. Foremost of the alarms that sound and/or are displayed is an alarm that signals when the value of the most recent reading is below or above user-set (or, if none, default) low or high limits, or if the trend exceeds the user-set default limits.

Power for the monitor is provided primarily through an ac power line 184 that drives an external power supply 186. An internal rechargeable nickel cadmium (NiCad) battery 188 is also included. In the event that line power is not available (e.g., during a power outage, or when moving the patient) the NiCad battery provides a minimum of four hours of monitor operation, provided the printer is not used. A lithium battery 190 is also included to maintain the monitor's memory and the time keeping function. Power supply control circuitry 192 selects and applies the appropriate power source to the other circuits of the monitor.

Further included within the monitor 34 is a touch sensitive screen 194 (also referred to as a "touchscreen"). The principal visual element of the monitor 34 is the display screen 168 which, with the touchscreen 194 positioned thereover, is touch sensitive. The screen presents a LCD graphic display of the glucose concentration and allows the user to give commands by touching areas on the screen called "buttons". Such buttons are rounded rectangles with white background and dark letters. There are various types of buttons, including menu option buttons, and data buttons. The menu option buttons change the screen to the selected option or make the monitor do whatever it has been asked to do. Data buttons allow the user to enter information into the monitor memory.

An analog-to-digital (A/D) converter 196 is used in conjunction with the touchscreen 194 in order to provide a digitized grid location whereat a touch of the touchscreen has been sensed. Such grid location is then compared to the known grid locations where the various buttons have been displayed in order to determine which button was touched. The use of touchscreens for entering information and selecting various options in this manner is particularly well suited for a medical device that may be used in a hospital setting, particularly an operating room (OR), because it eliminates the need for bulky keyboards that, in general, must be placed on a horizontal surface, and thereby occupy valuable working surface space.

A peripheral controller circuit further interfaces the microcomputer 160 with a wand port 200, a printer 202, and the sensor connector 204. The sensor connector 204, in turn, is connected to a potentiostat circuit 206 that controls the trim voltage $V_R$ applied to each sensor, and measures the currents $I_1$ and $I_2$ associated with each sensor. Such measurements are digitized by the potentiostat circuit 206, and provided to the microcomputer 160 for appropriate storage and processing.

An important requirement associated with operation of the monitor 34 is to assure that the proper calibration data for a given sensor assembly 32 is downloaded to the memory 164 for use by the microcomputer 160 as it computes the glucose concentration data. To this end, the wand port 200 allows a suitable sensor identifier wand 50 to read a sensor identifier button 48 that is included on the package 50 in which the sensor assembly is shipped, as seen in FIG. 9. In operation, the wand 46 is connected to the wand port 200. Each glucose sensor of the type that is not continually powered (i.e., those sensors that are not used with a contactless connector as shown in FIGS. 7A and 7B) typically has unique factory calibration parameters. These parameters are contained in a sealed stainless steel capsule, or sensor identifier 48. The sensor identifier 48 is mounted on the outer surface of the sensor package 50.

Figures 9A, 9B:
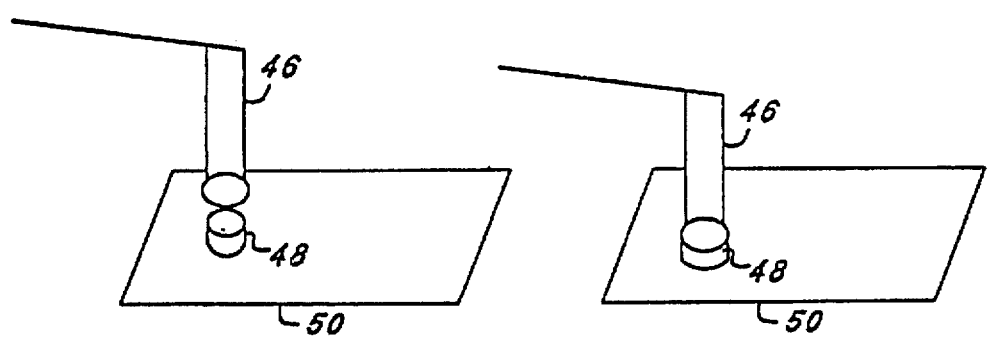
FIG. 9 depicts the manner in which a wand, coupled to the glucose monitor, determines the glucose sensor identification (ID) and calibration data when a particular sensor is first used within the glucose monitoring system.

The factory assigned serial number of the sensor assembly 32 must be entered into the monitor 34 before the system will operate. Such serial number is entered by touching the appropriate buttons on the menu screen. Once the serial number has been entered, it should be checked for accuracy.

and modified if needed. Once correct, the screen display changes and prompts the user to touch the wand 46 to the sensor identifier button 48 on the sensor package 50. Touching the wand to the sensor package is carried out as shown in FIG. 9. That is, the wand is placed above the identifier button 48, as shown in FIG. 9(A), and then placed over the button 48, as shown in FIG. 9(B). Touching the wand to the button 48 causes the wand to "read" the memory contained therewithin, thereby downloading the calibration data stored within the memory. If the serial number read through the wand matches the serial number that was entered manually, then the screen display advances to the next screen (entering patient ID information.)

Several of the menu screens that are displayed by the glucose monitor 34 are illustrated in FIGS. 10A–10E. The screens shown in FIGS. 10A–10E are not all the screens that may be displayed, but are merely representative of those screens that may be displayed. The various menu buttons on each screen are shown as rectangles with rounded corners. Other data displayed on the screens are shown as numbers.

Figure 10A:
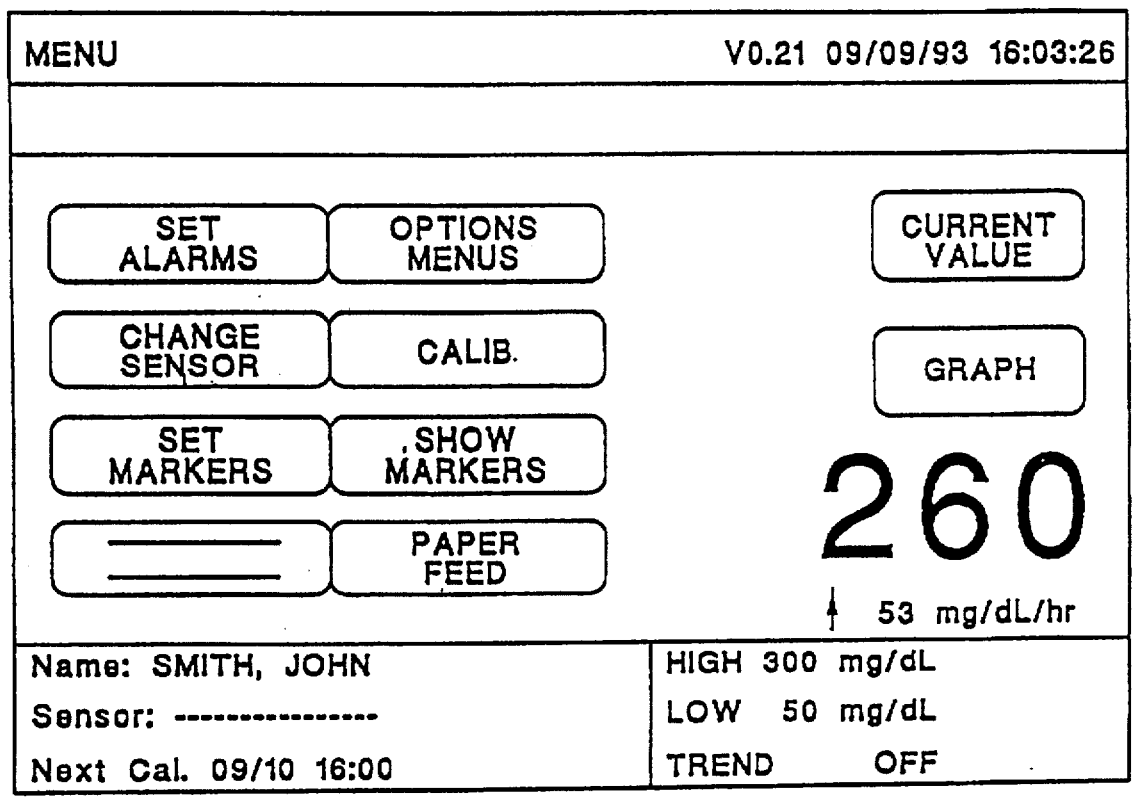
FIG. 10A shows the main menu screen displayed by the glucose monitor when in use.
Figure 10B:
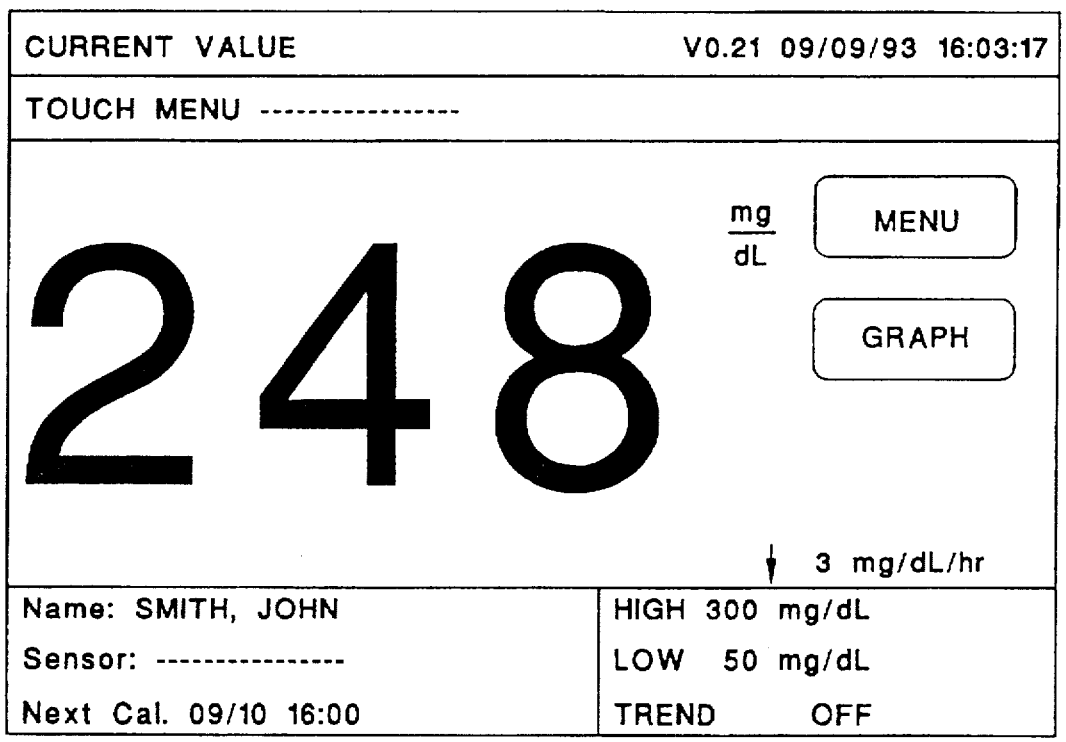
FIG. 10B depicts the current value screen displayed by the monitor when the current value selection is made from the main menu.
Figure 10C:
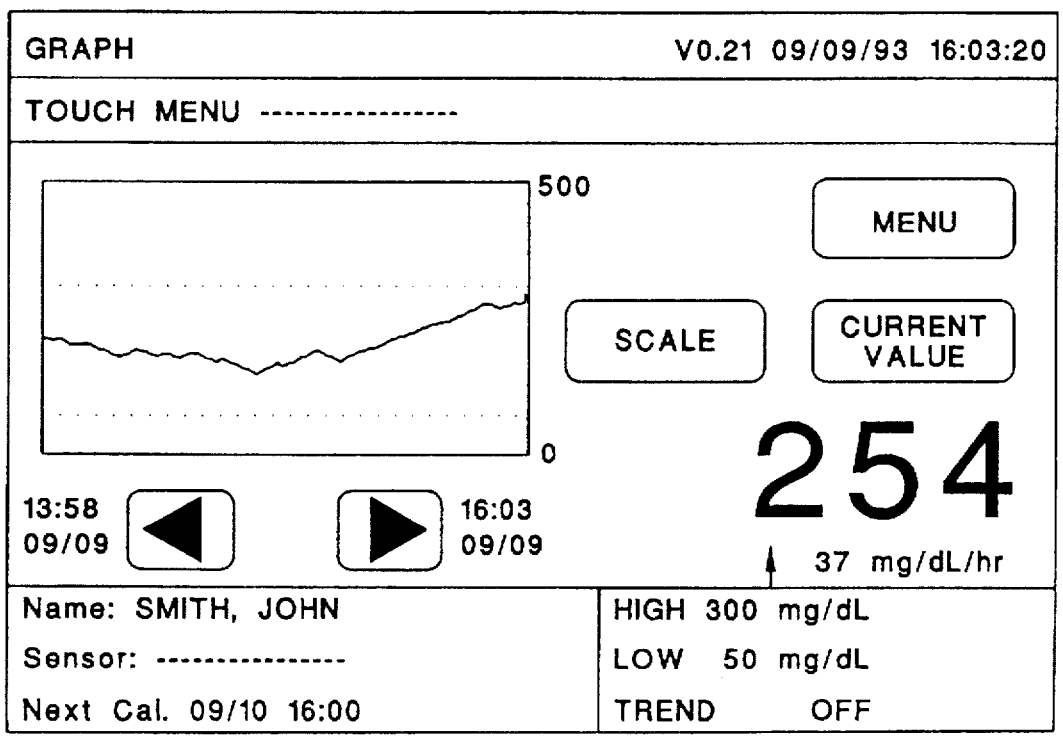
FIG. 10C depicts a representative graph of the glucose concentration that is generated and displayed by the glucose monitor when the graphic selection is made from the main menu.

FIG. 10A, for example, shows the main menu screen displayed by the glucose monitor when in use. FIG. 10B depicts the current value screen displayed by the monitor when the current value selection is made from the main menu. Note the large size of the glucose measurement displayed, providing easy-to-read numbers that are several inches high. FIG. 10C depicts a representative graph of the glucose concentration that is generated and displayed by the glucose monitor when the graphic selection is made from the main menu. A similar graph may be printed by the printer 202.

FIG. 10D shows a representative marker screen that is displayed by the glucose monitor when the marker selection is made from the main menu. Markers allow the user to specify at what time certain events occurred, such as sleeping, eating, exercising, and the like. The same information that appears on the marker screen may also be printed.

FIG. 10E illustrates the options menu screen that is displayed by the glucose monitor when the options selection is made from the main menu. Such options include, for example, the capability of choosing units, choosing a language, performing diagnostic and other tests, setting the date and clock, and the like.

As is evident from the above description, it is seen that the monitor 34 performs four basic functions: (1) system hardware setup, during which alarms are set, and during which time and date, units, language, and date format are established; (2) sensor introduction, during which the sensor is stabilized (for direct contact sensors), the sensor is identified, and the patient is identified; (3) system calibration, during which a blood or tissue sample is taken and time marked, with the blood sample result being input into the monitor so that appropriate sensor calibration may take place; and (4) patient monitoring, during which continuous monitoring of the concentration of a specified substance, e.g., glucose, of the patient is made, including 24 hour recalibration and 72 hour sensor replacement and calibration.

Figure 11:
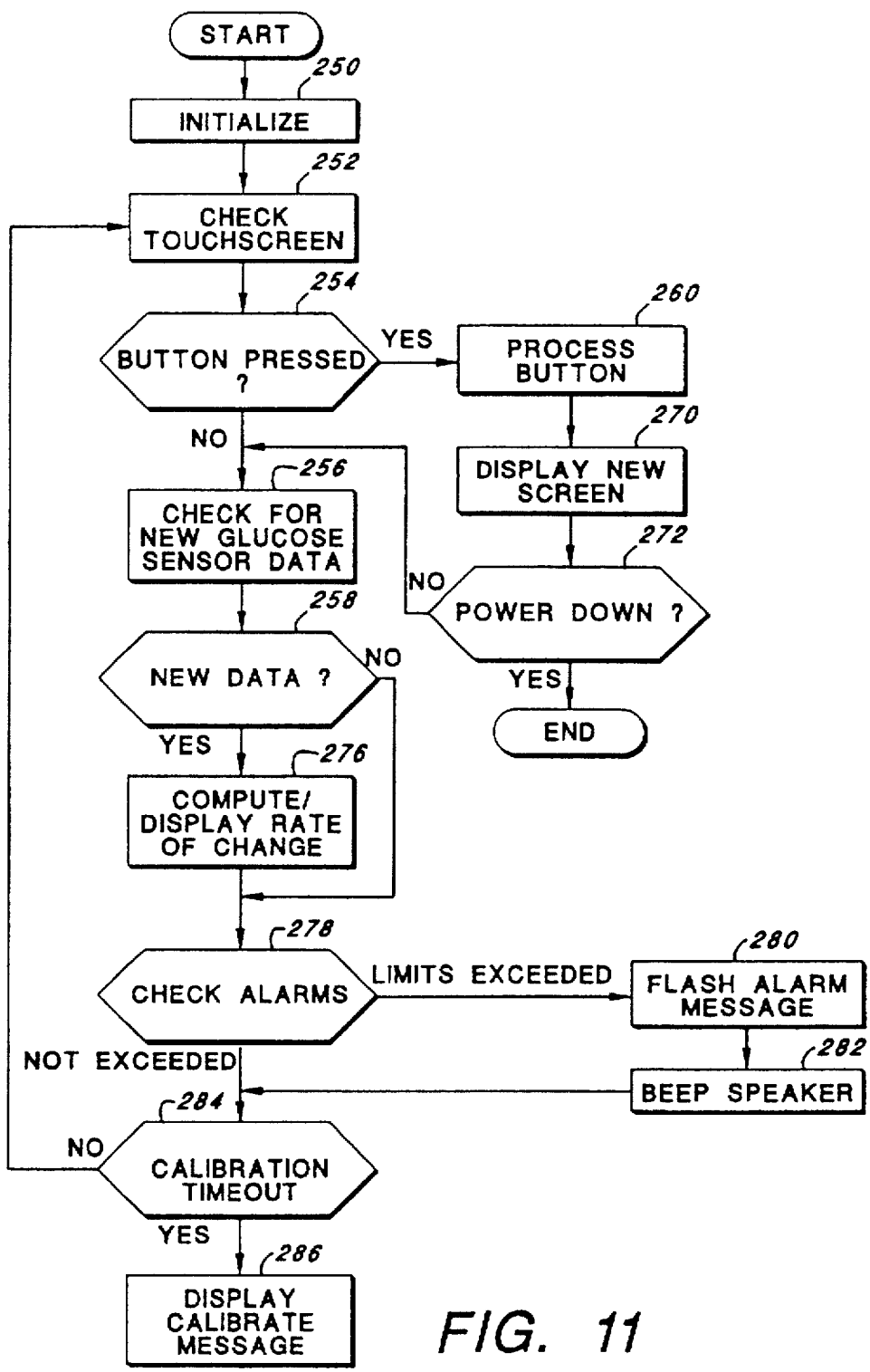
FIG. 11 shows a flow chart of the main loop of operation carried out by the glucose monitor.

Turning next to FIG. 11, there is shown a simplified flow chart of the main loop of operation carried out by microcomputer 160 as it performs its basic function of patient monitoring. In the flow chart of FIG. 11, each main step or process is depicted as a "box" or "block", with each box or block having a reference numeral for reference purposes. The main loop shown in FIG. 11 assumes that glucose is the substance being monitored and that the glucose monitoring system has already been initialized (block 250). Initialization includes a system hardware setup, during which the alarms are set, and the time and date, units, language, and date format are established. Further, initialization (block 250) includes sensor introduction, meaning that the sensor is stabilized (if needed), the sensor is identified, and the patient is identified. An initial system calibration is also performed during initialization (block 250) which involves drawing a blood or tissue glucose sample from the patient, measuring the glucose concentration in the sample using certifiable external equipment, imputing the measurement made into the system, and time marking when the sample was taken. The time marking is important so that the system knows when the next calibration must be performed. In general, the system signals that a new calibration is needed every 24 hours. If a recalibration is not made within 26 hours of the last calibration, then the monitoring system shuts down.

Once all the initialization steps have been completed, the main loop is entered. The main loop first checks the touchscreen (block 252). If a button on the touchscreen has been touched or pressed (YES branch of block 254), then such button is processed (block 260), meaning that whatever action is appropriate for the touched button is carried out. Such action always involves displaying a new screen (block 270), and may include other process steps (such as printing a graph, making a data calculation, or the like). If the new screen is a power-down screen (block 272), and if a power down operation is confirmed (YES branch of block 272), then the main loop terminates, and the monitoring system is powered OFF.

Regardless of whether a process button has been pressed (block 254), or whether a new screen has been displayed (block 270), the system next checks (assuming that the system remains powered) for new glucose sensor data (block 256). The glucose sensor, as explained above, is a continuous sensor. However, the currents $I_1$ and $I_2$ from each working electrode of each sensor (making four total current measurements) are only sampled every minute. Based on when the most recent sample has been taken, new glucose data may or may not be available (block 258). If it is available, then such data is retrieved and displayed (block 274).

Based on the new or old glucose data, each pass through the main loop also involves a computation and display of the rate of change or "trend" of the glucose data (block 276). The glucose data, including the computed rate of change is compared to the limits associated with the alarms (block 278). If any of the alarm limits have been exceeded, then an alarm message is flashed on the screen (block 280), and the monitor beeps (block 282). The beeping can be silenced by touching a silence button on the screen, but the flashing alarm message continues until such time as the condition which triggered the alarm is corrected as evidenced by new sensor data.

The alarms are preferably programmable to be different in positive or negative directions, including different rate-of-change alarms for a positive (increasing) change in concentration of the substance being monitored and a negative (decreasing) change in the concentration. This is because, e.g., a sudden negative change in glucose concentration, particularly if starting from an already low level of glucose concentration, can be far more serious than a positive change in glucose concentration, or a negative change that starts from a higher glucose concentration. Hence, the alarm limits may be set to identify the potentially more dangerous low glucose concentration levels, and negative rate of change levels that start from a low level.

In some embodiments of the invention, however, the alarm limits may be symmetrical, without regard to whether the change is positive or negative.

Finally, each time through the main loop shown in FIG. 11, a determination is made as to whether it is time to recalibrate (block 284). Recalibration should be performed every 24 hours, and must be performed within 26 hours of the last calibration. If it is time to recalibrate, then a calibration message is displayed (block 286) and the calibration loop is initiated.

Figure 12:
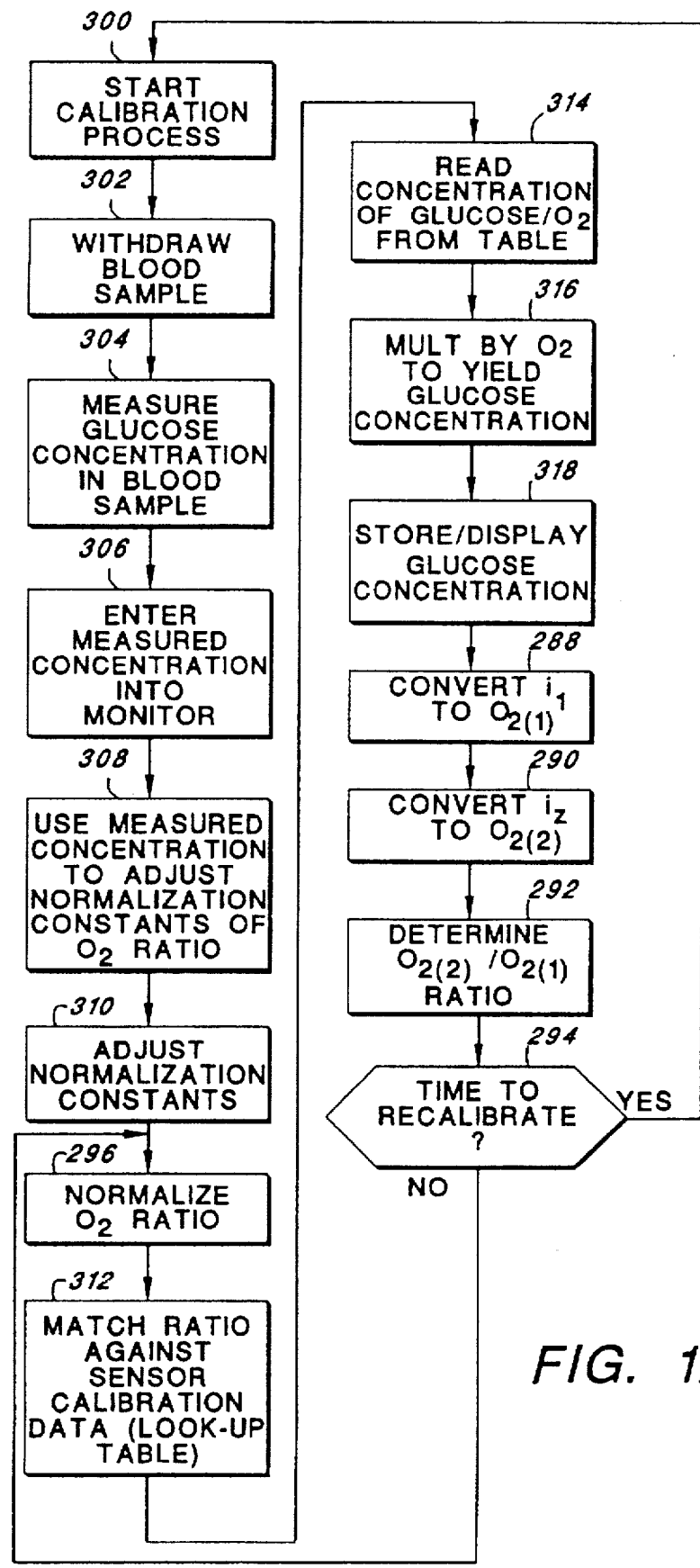
FIG. 12 is a flow chart of the calibration method used by the glucose monitoring system.

A simplified flow diagram of the calibration loop for a glucose sensor is shown in FIG. 12. Essentially, the calibration loop is a single point calibration method, meaning that only a single point of glucose data from an external source is needed to perform the calibration method.

Turning to FIG. 12, when the calibration process is started (block 300), then the user is instructed to withdraw a blood or other tissue/fluid sample from the patient (block 302). Such sample is then subjected to a conventional off-line measurement device, and a reading is obtained (block 304). The off-line reading is then entered into the monitor (block 306) using a special touchscreen display for such purpose. Such entered value is then used to adjust the normalization constants of the $O_2$ ratio used in computing the concentration (block 308), explained below.

During the normal measurement loop, as indicated at the right of FIG. 12, the current measurements from each sensor, assuming each sensor is a glucose sensor, are obtained and converted to an $O_2$ measurement. There are actually four current measurements involved, two for each sensor, even though only two current measurements are shown in FIG. 12. The first current measurement $I_1$ is converted to an appropriate $O_2(1)$ measurement (block 288). Similarly, the second current measurement $I_2$ is converted to an $O_2(2)$ measurement (block 290). A ratio is then determined of $O_2(2)/O_2(1)$ (block 292). This ratio must be normalized to match the most recent external glucose reading. If it is time to recalibrate (YES branch of block 294), then such calibration is performed by obtaining the external glucose reading based on a drawn blood sample, as described above. Appropriate normalization constants, determined from the external glucose measurement (block 310) are then used to normalize the $O_2$ ratio (block 296). If it is not time to recalibrate (NO branch of block 294), then the most recently determined normalization constants are used for the normalization of the $O_2$ ratio (block 296).

The normalized $O_2$ ratio is then matched against sensor calibration data (block 312) obtained from the factory for the particular sensors that are used. Such calibration data is essentially available in a look-up table that is downloaded to the monitor at the time of initialization using the data wand as described previously. Once the best match is found, then the glucose/$O_2$ ratio may be determined (block 314). This ratio is multiplied by the measured $O_2$ value (block 316), thereby leaving just the glucose concentration. Such glucose concentration is then stored in the monitor memory, and displayed, as appropriate.

From the preceding description, it is thus seen that the present invention provides a monitoring system that continuously monitors the glucose concentration, or the concentration of another substance, of a patient, providing real-time readings and a history of the concentration of the measured substance, including the rate at which the concentration is changing. It is further seen that the invention provides a way to graphically display the measured concentration, and/or the rate of change of such concentration, in large, easy-to-read numerals or graphs in a format that cannot easily be misunderstood or misinterpreted. Further, the monitoring system thus provided has setable limits above or below which the measured concentration, or the rate of change (trend) of the concentration, may not go without flashing and/or sounding an alarm.

As also seen from the above, the present invention provides a glucose sensor designed for placement into a patient's venous system or other body location so as to continuously monitor in-line the glucose concentration in the patient without the need for withdrawing a blood or tissue sample (except for an occasional, e.g., once every 24 hours, calibration check). The glucose concentration measurement is provided by means of sensor signals that comprise electrical signals (electrical currents). From such electrical signals, the glucose concentration is easily derived using calibration data generated during manufacture of the sensor, as well as the calibration check data obtained once every 24 hours.

It is further seen that the invention provides, in one embodiment thereof, a monitoring system that couples a sensor placed into the venous system, or other body location, of the patient with a monitor through a contactless connector. Such contactless connector advantageously allows for the inadvertent or purposeful disconnection of the monitor from the sensor without harming the patient or the sensor, and without disrupting operation of the sensor (thereby preventing the need for recalibration of the sensor).

Also, it is evident from the above description that the invention provides a monitoring system that utilizes measurements from a plurality of venous or other implanted sensors in order to confirm the correctness of a given determination or measurement.

While the invention herein disclosed has been described by means of specific embodiments and applications thereof, numerous modifications and variations could be made thereto by those skilled in the art without departing from the scope of the invention set forth in the claims.

What is claimed is:

1. A glucose monitoring system comprising:
an enzymatic glucose sensor adapted to be placed within a person whose blood glucose concentration is to be measured, said glucose sensor including means for generating a sensor signal that varies inversely proportional to the concentration of sensed glucose, said glucose sensor comprising an oxygen detector that detects the amount of oxygen in the region of a prescribed enzyme held within said glucose sensor, and wherein glucose and oxygen react with said prescribed enzyme such that the amount of oxygen is inversely proportional to the glucose concentration, and wherein said oxygen detector comprises
a first working electrode, a counter electrode, a reference electrode, and a second working electrode, all of said first and second working electrodes, reference electrode and counter electrode being enclosed within a first membrane wherein an ionic solution is maintained, and said first membrane being enclosed within a second membrane,
said prescribed enzyme being confined to a window region near said first working electrode,
electrical means for causing an electrical current to flow between said counter electrode and said first and second working electrodes, and
means for measuring how much current flows from said first and second working electrodes when a prescribed trim voltage is maintained across said reference electrode and said first and second working electrodes;

sensor signal comprises the ratio of said currents, thereby providing a measure of oxygen in the vicinity of said glucose sensor; and a glucose monitor electrically coupled to the glucose sensor, said monitor comprising means for receiving the sensor signal from the signal generating means, means for processing the sensor signal and generating a glucose concentration data signal therefrom, means for storing the glucose concentration data signal, means for monitoring the glucose concentration data signal over a prescribed period of time and generating a rate of change signal that indicates how rapidly the glucose concentration data signal is changing, means for selectively displaying the glucose concentration data signal and the rate of change signal, first alarm means for determining if the glucose concentration data signal exceeds a preset level limit, and if so, generating a first alarm signal, second alarm means for determining if the rate of change signal exceeds a preset trend limit, and if so, generating a second alarm signal, calibration means for periodically calibrating the sensor so that it provides an accurate measure of the glucose concentration in the blood stream, and control means for controlling the monitor so that it performs at least one of a plurality of monitoring functions as selected by a user of said monitor.

2. The glucose monitoring system as set forth in claim 1 wherein said prescribed enzyme comprises glucose oxidase.

3. The glucose monitoring system as set forth in claim 1 wherein said calibration means includes means for normalizing a ratio of said currents with a calibration constant, said calibration constant being obtained from an independent measure of the glucose concentration in a tissue/fluid sample taken from the patient.

4. The glucose monitoring system as set forth in claim 3 wherein said glucose monitor further includes means for issuing a calibration message in the event said independent measure of the glucose in the tissue/fluid sample has not been taken within a prescribed period from a prior calibration.

5. The glucose monitoring system as set forth in claim 3 wherein said calibration means further includes means for downloading calibration data to said glucose monitor at the time that a particular glucose sensor is first coupled to said glucose monitor, said calibration data being generated at the time of manufacture of said glucose sensor.

6. The glucose monitoring system as set forth in claim 1 wherein said glucose monitor includes a flat display of at least four inches by four inches overlaid with a touch sensitive screen, and wherein said control means comprises means for displaying one of a plurality of menus on said display, each of said plurality of menus including at least one button labeled with a monitoring function, and wherein said touch sensitive screen includes means for sensing if said display is touched by a user of said glucose monitor at a button of said menu, and if so, carrying out the function specified by said button.

7. The glucose monitoring system as set forth in claim 6 wherein said means for displaying further comprises at least one button for displaying the glucose concentration data signal in large numbers that substantially fill said flat display.

8. The glucose monitoring system as set forth in claim 1 wherein said glucose sensor is electrically coupled to said glucose monitor through a coupling cable that provides direct electrical contact between the glucose monitor and the glucose sensor.

9. The glucose monitoring system as set forth in claim 8 wherein said glucose sensor is coupled to said glucose monitor through a contactless coupling that electrically isolates said glucose sensor from said glucose monitor.

10. The glucose monitoring system as set forth in claim 9 wherein said contactless coupling comprises a transformer coupling.

11. The glucose monitoring system as set forth in claim 9 wherein said contactless coupling comprises an optical coupling.

12. The glucose monitoring system as set forth in claim 9 wherein said contactless coupling includes signal processing means on a sensor side of said coupling, said signal processing means including means for encoding the sensor signals passed through to the glucose monitor with sensor source information, whereby all of the sensor signals passed through to the glucose monitor may share a common set of cables.

13. The glucose monitoring system as set forth in claim 12 wherein said contactless coupling further includes a memory element having calibration data stored therein unique to said sensors, and a battery on the sensor side of said coupling, said battery providing a source of continuous power to said sensors.

14. The glucose monitoring system as set forth in claim 13 wherein said contactless coupling includes at least one magnet and a metal member to which said magnet is attracted, the magnet or metal member being located on the sensor side of the coupling, and the other of the magnet or metal member being located on a monitor side of the coupling, said magnet having a magnetic force field that pulls the magnet toward the metal member, said magnetic force field thereby holding said contactless coupling together.

15. A glucose monitoring system comprising:

a glucose assembly comprising a plurality of glucose sensors, each glucose sensor comprising an enzymatic glucose sensor adapted to be positioned within a person whose glucose concentration is to be measured, each glucose sensor of the glucose assembly providing a respective sensor signal that varies as a function of sensed glucose; and a glucose monitor electrically coupled to the glucose assembly, said glucose monitor comprising means for receiving the sensor signal from each glucose sensor, means for processing the sensor signal received from each glucose sensor, said means for processing including means for comparing the sensor signals obtained from each of said plurality of sensors and generating a composite sensor signal only if the respective sensor signals are within a first prescribed amount of each other, means for storing the composite sensor signal, means for monitoring the composite sensor signal over a prescribed period of time and generating a rate of change signal that indicates how rapidly the composite sensor signal is changing, means for selectively displaying the composite sensor signal and the rate of change signal, first alarm means for determining if the composite sensor signal exceeds a preset level limit, and if so, generating a first alarm signal, second alarm means for determining if the rate of change signal exceeds a preset trend limit, and if so, generating a second alarm signal, calibration means for periodically verifying that each glucose sensor of the sensor assembly provides an accurate measure of the glucose concentration in the blood stream, and control means for controlling the monitor so that it performs at least one of a plurality of monitoring functions as selected by a user of said monitor.

16. The glucose monitoring system as set forth in claim 15 wherein said processing means further includes means for generating an error message in the event that the respective sensor signals are not within said first prescribed amount of each other, said error message advising a user of said glucose monitor to check said plurality of glucose sensors.

17. The glucose monitoring system as set forth in claim 16 wherein said processing means further includes shutdown means for automatically shutting down said glucose monitor in the event at least one of the sensor signals differs from the others of said sensor signals by more than a second prescribed amount.

18. The glucose monitoring system as set forth in claim 15 further including at least one additional sensor adapted to sense a parameter other than glucose concentration, and wherein said processing means includes means for combining all of the sensor signals in arriving at said composite sensor signal.

19. A method of measuring a glucose concentration in a patient comprising:

(a) inserting a plurality of glucose sensor assemblies into a patient, each of said glucose sensor assemblies having a reference electrode, a counter electrode and first and second working electrodes;

(b) applying a voltage to said electrodes so as to cause first and second electrical currents to flow through said first and second working electrodes, respectively, and measuring said first and second electrical currents, the ratio of said second electrical current to said first electrical current providing a measure of oxygen in the patient;

(c) placing a glucose oxidase enzyme at said first working electrode, said glucose oxidase enzyme reacting with the oxygen and glucose such that the amount of oxygen measured at said first electrode is inversely proportional to the glucose concentration;

(d) determining the glucose concentration based on said measure of oxygen and calibration constants associated with each of said glucose sensors;

(e) comparing the glucose concentration measured by each of said plurality of sensors to determine if the respective plurality of glucose concentration measurements are within a prescribed percentage of each other, and if so, combining the plurality of glucose concentration measurements to form a composite glucose measurement, and if not, rejecting the plurality of glucose measurements as being inaccurate;

(f) storing the composite glucose measurement as a function of time;

(g) computing a rate-of-change signal for the composite glucose measurement that indicates how said composite glucose measurement has varied over a specified period of time;

(h) comparing the composite glucose measurement formed most recently and the rate-of-change signal to preprogrammed limits, and generating an alarm signal in the event the preprogrammed limits are exceeded; and (i) selectively displaying the composite glucose measurement and rate-of-change signal.

20. The method, as set forth in claim 19, wherein said glucose assembly is inserted into the peritoneal system of the patient.

21. The method, as set forth in claim 19, wherein said glucose assembly is placed in contact with body tissue of the patient.

22. A patient monitoring system comprising:

an enzymatic sensor adapted to be inserted into a patient in order to make contact between said sensor and a bodily fluid/tissue of said patient, said sensor including means for generating a sensor signal that varies as a function of concentration of a substance sensed in said bodily fluid/tissue, said sensor comprising a detector that detects the amount of said substance in the region of a prescribed enzyme held within said sensor, and wherein said substance in said bodily fluid/tissue reacts with said prescribed enzyme such that the amount of said substance can be measured, and wherein said detector comprises a first working electrode, a counter electrode, a reference electrode, and a second working electrode, all of said first and second working electrodes, reference electrode and counter electrode being enclosed within a first membrane wherein an ionic solution is maintained, and said first membrane being enclosed within a second membrane, said prescribed enzyme being confined to a window region near said first working electrode, electrical means for causing an electrical current to flow between said counter electrode and said first and second working electrodes, and means for measuring how much current flows from said first and second working electrodes when a prescribed trim voltage is maintained across said reference electrode and said first and second working electrodes, said measuring means being in communication with said sensor signal generating means, the sensor signal comprising the ratio of said currents and being representative of the substance concentration in said bodily fluid/tissue in the vicinity of said sensor; and a monitor electrically coupled to the sensor, said monitor comprising means for receiving the sensor signal, means for processing the sensor signal and generating a substance concentration data signal therefrom, means for storing the substance concentration data signal, means for monitoring the substance concentration data signal over a prescribed period of time and generating a rate of change signal that indicates how rapidly the substance concentration data signal is changing, means for selectively displaying the substance concentration data signal and the rate of change signal, first alarm means for determining if the substance concentration data signal exceeds a preset level limit, and if so, generating a first alarm signal, second alarm means for determining if the rate of change signal exceeds a preset trend limit, and if so, generating a second alarm signal, calibration means for periodically calibrating the sensor so that it provides an accurate measure of the substance concentration in the bodily fluid/tissue, and control means for controlling the monitor so that it performs at least one of a plurality of monitoring functions as selected by a user of said monitor.

23. A method of measuring the concentration level of a particular substance within a patient, said method comprising the steps of:
  (a) inserting a plurality of sensors into a body location of a patient in order to make contact between said plurality of sensors and body fluid/tissue of the patient, each of said sensors having a reference electrode, a counter electrode and first and second working electrodes, and means for providing a measure of a substance concentration within the patient's body fluid/tissue as a function of the electrical current flowing between said first and second working electrodes;
  (b) applying a voltage to said electrodes so as to cause first and second electrical currents to flow through said first and second working electrodes, respectively, and measuring said first and second electrical currents, said first and second electrical currents providing a measure of the substance concentration within the patient's body fluid/tissue;
  (c) determining the substance concentration in the body fluid/tissue of the patient based on the first and second electrical currents measured in step (b) for each of said plurality of sensors; and
  (d) comparing the substance concentration measured by each of said plurality of sensors to determine if the respective plurality of substance concentration measurements are within a prescribed percentage of each other, and if so, combining the plurality of substance concentration measurements to form a composite substance measurement, and if not, rejecting the plurality of substance measurements as being inaccurate.

24. The method of claim 23 further including:
  (a) storing the composite substance measurement as a function of time;
  (b) computing a rate-of-change signal for the composite substance measurement that indicates how said composite substance measurement has varied over a specified period of time;
  (c) comparing the composite substance measurement formed most recently and the rate-of-change signal to preprogrammed limits, and generating an alarm signal in the event the preprogrammed limits are exceeded; and
  (d) selectively displaying the composite substance measurement and rate-of-change signal.

25. An enzymatic sensor adapted to be inserted into a patient in order to make contact with body fluid/tissue of said patient, said sensor comprising:
  a first working electrode (W1), a counter electrode (C), a reference electrode (R), and a second working electrode (W2), all of said first and second working electrodes, reference electrode and counter electrode being enclosed within a first membrane wherein an ionic solution is maintained, and said first membrane being enclosed within a second membrane,
  said prescribed enzyme being confined to a window region near said first working electrode,
  electrical means for causing an electrical current to flow between said counter electrode and said first and second working electrodes, and
  means for measuring how much current flows from said first and second working electrodes when a prescribed trim voltage is maintained across said reference electrode and said first and second working electrodes, a ratio of said currents comprising a sensor signal, which sensor signal provides a measure of the substance concentration in said body fluid/tissue in the vicinity of said sensor.

26. A sensor assembly adapted for implantation into the body of a patient to measure the concentration of one or more substances in the patient's blood, said sensor assembly comprising:
  a substrate;
  first and second sets of sensors spaced apart on said substrate, wherein each set of sensors comprises:
    first and second working electrodes bonded to said substrate;
    a reference electrode bonded to said substrate;
    a counter electrode bonded to said substrate; and
    means for making electrical contact with said first and second working electrodes, reference electrode, and counter electrode;
    a layer of insulation deposited on said substrate and means for making electrical contact so as to be interspersed between the electrodes bonded to said substrate, a prescribed surface area of each of said electrodes being exposed through said layer of insulation, whereby said first and second working electrodes, reference electrode and counter electrode are all electrically isolated from each other on said substrate;
    first membrane means covering said substrate and electrodes;
    a saline solution held within said first membrane, said saline solution being in contact with said electrodes bonded to said substrate;
    second membrane means covering said first membrane means, said second membrane means having a window pocket therein above the exposed surface area of said first working electrode;
    a prescribed enzyme placed within said window pocket; and
  means for applying a prescribed reference voltage, within each set of sensors, between said counter electrode and said reference electrode, and between said first and second working electrodes and said reference electrode, and for measuring the electrical current that flows from said first and second working electrodes, within each set of sensors;
  whereby when said sensor assembly is inserted in the patient's venous system, oxygen and other substances in the blood of the patient may penetrate said first and second membrane means of each set of sensors and electrochemically react, in the presence of the prescribed enzyme held in said window pocket of each set of sensors, with the current flowing through each of said first working electrodes, and electrochemically react in the absence of said enzyme with the current flowing through each of said second working electrodes;
  said currents flowing through said first and second working electrodes of each set of sensors thereby providing a measure of oxygen and other substances in the blood of the patient as a function of the electrochemical reactions that occur at said first and second working electrodes of each set of sensors.

27. The sensor assembly as set forth in claim 26 wherein said prescribed enzyme comprises glucose oxidase.

28. The sensor assembly as set forth in claim 26, wherein said first and second sets of sensors are separated on said substrate such that the window pockets are spaced apart about 0.4 to 1.0 inches along the length of the substrate.

29. The sensor assembly as set forth in claim 26 wherein said first and second sets of sensors further comprise a temperature sensor mounted on said substrate.

30. The sensor assembly as set forth in claim 29 wherein each of said temperature sensors comprises a prescribed semiconductor having a resistivity that varies as a function of temperature, and means for applying a voltage across said semiconductor, whereby the current flowing through said semiconductor provides a measure of the resistivity, and hence the temperature.

31. The sensor assembly as set forth in claim 29 further including a cable carrying sufficient electrical conductors to make contact with said first and second electrodes, reference electrode, counter electrode and temperature sensor of each of said sets of sensors, said cable terminating in a first contactless connector, said first contactless connector having a battery and a control chip therein that receives and processes the electrical current that flows from the first and second working electrodes of each set of sensors, said control chip including memory means for storing calibration data associated with said sensor assembly, processing means for processing the received electrical current with the calibration data to produce encoded sensor data signals, and transmitting means for transmitting the encoded sensor data signals to a receiver located in a second contactless connector, said second contactless connector being adapted to be coupled to said first contactless connector without making direct electrical contact therewith, whereby electrical isolation is provided between the first and second contactless connectors, said second contactless connector being coupled to a monitoring device whereat said encoded sensor data signals are decoded, displayed and stored.

32. The sensor assembly as set forth in claim 31 wherein said second contactless connector is coupled to said monitoring device through a connection cable having two electrical conductors.

33. The sensor assembly as set forth in claim 31 wherein at least one of said first and second contactless connectors includes a permanent magnet that is attracted to a metallic member in the other contactless connector, and wherein said permanent magnet provides a holding force for maintaining said first and second contactless connectors in close proximity to each other.

* * * * *